(12) United States Patent
Maples et al.

(10) Patent No.: US 9,689,031 B2
(45) Date of Patent: *Jun. 27, 2017

(54) NICKING AND EXTENSION AMPLIFICATION REACTION FOR THE EXPONENTIAL AMPLIFICATION OF NUCLEIC ACIDS

(75) Inventors: Brian K. Maples, Lake Forest, CA (US); Rebecca C. Holmberg, Cardiff, CA (US); Andrew P. Miller, San Diego, CA (US); Jarrod W. Provins, Dana Point, CA (US); Richard B Roth, San Diego, CA (US); Jeffrey G. Mandell, La Jolla, CA (US)

(73) Assignee: Ionian Technologies, Inc., San Diego, CA (US)

( * ) Notice: Subject to any disclaimer, the term of this patent is extended or adjusted under 35 U.S.C. 154(b) by 3 days.

This patent is subject to a terminal disclaimer.

(21) Appl. No.: 11/778,018

(22) Filed: Jul. 14, 2007

(65) Prior Publication Data

US 2009/0017453 A1    Jan. 15, 2009

(51) Int. Cl.
*C12Q 1/68*    (2006.01)

(52) U.S. Cl.
CPC ........... *C12Q 1/686* (2013.01); *C12Q 1/6844* (2013.01)

(58) Field of Classification Search
USPC ....................................................... 435/6.12
See application file for complete search history.

(56) References Cited

U.S. PATENT DOCUMENTS

| | | | |
|---|---|---|---|
| 5,210,015 A | 5/1993 | Gelfand et al. | |
| 5,270,184 A | 12/1993 | Walker et al. | |
| 5,354,668 A | 10/1994 | Auerbach | |
| 5,397,698 A | 3/1995 | Goodman et al. | |
| 5,422,252 A | 6/1995 | Walker et al. | |
| 5,455,166 A | 10/1995 | Walker | |
| 5,470,723 A | 11/1995 | Walker et al. | |
| 5,487,972 A | 1/1996 | Gelfand et al. | |
| 5,556,751 A | 9/1996 | Stefano | |
| 5,591,609 A | 1/1997 | Auerbach | |
| 5,614,387 A | 3/1997 | Shen et al. | |
| 5,614,389 A | 3/1997 | Auerbach | |
| 5,648,211 A | 7/1997 | Fraiser et al. | |
| 5,681,705 A | 10/1997 | Schram et al. | |
| 5,712,124 A | 1/1998 | Walker | |
| 5,733,733 A | 3/1998 | Auerbach | |
| 5,736,365 A | 4/1998 | Walker et al. | |
| 5,744,311 A | 4/1998 | Frasier et al. | |
| 5,747,246 A | 5/1998 | Pannetier et al. | |
| 5,747,255 A | 5/1998 | Brenner | |
| 5,804,375 A | 9/1998 | Gelfand et al. | |
| 5,834,202 A | 11/1998 | Auerbach | |
| 5,834,254 A | 11/1998 | Shen et al. | |
| 5,840,487 A | 11/1998 | Nadeau et al. | |
| 5,846,717 A | 12/1998 | Brow et al. | |
| 5,916,779 A | 6/1999 | Pearson et al. | |
| 5,928,869 A | 7/1999 | Nadeau et al. | |
| 5,942,391 A | 8/1999 | Zhang et al. | |
| 5,985,557 A | 11/1999 | Prudent et al. | |
| 6,033,881 A | 3/2000 | Himmler et al. | |
| 6,040,166 A | 3/2000 | Erlich et al. | |
| 6,063,604 A * | 5/2000 | Wick et al. | 435/91.2 |
| 6,077,669 A | 6/2000 | Little et al. | |
| 6,087,133 A | 7/2000 | Dattagupta et al. | |
| 6,090,552 A | 7/2000 | Nazarenko et al. | |
| 6,110,677 A | 8/2000 | Western et al. | |
| 6,130,038 A | 10/2000 | Becker et al. | |
| 6,191,267 B1 * | 2/2001 | Kong et al. | 536/23.4 |
| 6,214,587 B1 | 4/2001 | Dattagupta et al. | |
| 6,251,600 B1 | 6/2001 | Winger et al. | |
| 6,261,768 B1 | 7/2001 | Todd et al. | |
| 6,294,337 B1 | 9/2001 | Hayashizaki | |
| 6,316,200 B1 | 11/2001 | Nadeau et al. | |
| 6,335,164 B1 | 1/2002 | Kigawa et al. | |
| 6,348,314 B1 | 2/2002 | Prudent et al. | |
| 6,350,580 B1 | 2/2002 | Sorge | |
| 6,372,434 B1 | 4/2002 | Weissman et al. | |
| 6,403,341 B1 | 6/2002 | Barnes et al. | |
| 6,423,495 B1 | 7/2002 | Oultram et al. | |
| 6,482,590 B1 | 11/2002 | Ullman et al. | |
| 6,566,103 B2 | 5/2003 | Wijnhoven et al. | |
| 6,632,611 B2 | 10/2003 | Su et al. | |
| 6,656,680 B2 | 12/2003 | Nadeau et al. | |
| 6,660,475 B2 | 12/2003 | Jack et al. | |
| 6,686,150 B1 | 2/2004 | Blackburn et al. | |
| 6,692,917 B2 | 2/2004 | Neri et al. | |

(Continued)

FOREIGN PATENT DOCUMENTS

| CN | 1850981 | 10/2006 |
|---|---|---|
| EP | 2657350 | 10/2013 |

(Continued)

OTHER PUBLICATIONS

Van Ness et al., Isothermal reactions for the amplification of oligonucleotides, pp. 4504-4509 _PNAS _Apr. 15, 2003 _vol. 100 _No. 8.*

Hite et al., Factors affecting fidelity of DNA synthesis during PCR amplification of d(C-A)n .d(G-T)n microsatellite repeats, Nucleic Acids Research, 1996, vol. 24, No. 12, pp. 2429-2434.*

Buck et al., Research Report, Design Strategies and Performance of Custom DNA Sequencing Primers BioTechniques 27:528-536 (Sep. 1999).*

Van Ness J, Van Ness LK, Galas DJ. Isothermal reactions for the amplification of oligonucleotides. Proc Natl Acad Sci U S A. Apr. 15, 2003; 100(8):4504-9. Epub Apr. 4, 2003.*

(Continued)

*Primary Examiner* — Angela M Bertagna
*Assistant Examiner* — Olayinka Oyeyemi
(74) *Attorney, Agent, or Firm* — Fish & Richardson P.C.

(57) ABSTRACT

The invention is in general directed to the rapid exponential amplification of short DNA or RNA sequences at a constant temperature.

16 Claims, 19 Drawing Sheets

(56) References Cited

U.S. PATENT DOCUMENTS

| | | | |
|---|---|---|---|
| 6,713,297 B2 | 3/2004 | McMillan et al. | |
| 6,743,582 B2 | 6/2004 | Nadeau et al. | |
| 6,767,724 B2 | 7/2004 | Lee et al. | |
| 6,811,971 B2 | 11/2004 | Klepp et al. | |
| 6,861,222 B2 | 3/2005 | Ward et al. | |
| 6,884,586 B2 | 4/2005 | Van Ness et al. | |
| 6,893,819 B1 | 5/2005 | Sorge | |
| 6,929,915 B2 | 8/2005 | Benkovic et al. | |
| 6,958,217 B2 | 10/2005 | Pedersen | |
| 6,977,148 B2 | 12/2005 | Dean et al. | |
| 7,074,600 B2 | 7/2006 | Dean et al. | |
| 7,112,423 B2 | 9/2006 | Van Ness et al. | |
| 7,270,981 B2 | 9/2007 | Armes et al. | |
| RE39,885 E | 10/2007 | Nadeau et al. | |
| 7,276,597 B2 | 10/2007 | Sorge | |
| 7,297,485 B2 | 11/2007 | Bornarth et al. | |
| 7,309,573 B2 | 12/2007 | Sorge | |
| 7,399,590 B2 | 7/2008 | Piepenburg et al. | |
| 7,972,820 B2 | 7/2011 | Mayer | |
| 2002/0042059 A1 | 4/2002 | Makarov et al. | |
| 2002/0150919 A1 | 10/2002 | Weismann et al. | |
| 2003/0082590 A1 | 5/2003 | Van Ness | |
| 2003/0138800 A1* | 7/2003 | Van Ness et al. | 435/6 |
| 2003/0165911 A1 | 9/2003 | Van Ness et al. | |
| 2004/0038256 A1 | 2/2004 | Van Ness et al. | |
| 2004/0058349 A1 | 3/2004 | Van Ness et al. | |
| 2004/0058378 A1 | 3/2004 | Kong | |
| 2005/0009050 A1 | 1/2005 | Nadeau et al. | |
| 2005/0042601 A1 | 2/2005 | Wolfe | |
| 2005/0112639 A1 | 5/2005 | Wang et al. | |
| 2005/0147973 A1 | 7/2005 | Knott | |
| 2005/0164207 A1 | 7/2005 | Shapero | |
| 2005/0202490 A1 | 9/2005 | Makarov et al. | |
| 2005/0233332 A1 | 10/2005 | Collis | |
| 2005/0266417 A1 | 12/2005 | Barany et al. | |
| 2006/0154286 A1 | 7/2006 | Kong | |
| 2006/0160759 A1 | 7/2006 | Chen et al. | |
| 2006/0257860 A1 | 11/2006 | Marlowe et al. | |
| 2007/0020639 A1 | 1/2007 | Shapero | |
| 2007/0031857 A1 | 2/2007 | Makarov et al. | |
| 2008/0038782 A1 | 2/2008 | Borns | |
| 2008/0096257 A1 | 4/2008 | Yao et al. | |
| 2009/0081670 A1 | 3/2009 | Maples et al. | |
| 2009/0111089 A1 | 4/2009 | Lindstrom et al. | |
| 2010/0184205 A1 | 7/2010 | Bentwich et al. | |
| 2010/0204297 A1 | 8/2010 | Chen et al. | |

FOREIGN PATENT DOCUMENTS

| | | | |
|---|---|---|---|
| EP | 2660333 | 11/2013 | |
| EP | 2824189 | 1/2015 | |
| GB | 2416352 | 1/2006 | |
| WO | WO94/03635 | 2/1997 | |
| WO | WO 98/39485 | 9/1998 | |
| WO | WO 99/07409 | 2/1999 | |
| WO | WO 99/32619 | 7/1999 | |
| WO | WO 00/01846 | 1/2000 | |
| WO | WO 00/28084 | 5/2000 | |
| WO | WO 00/44895 | 8/2000 | |
| WO | WO 00/44914 | 8/2000 | |
| WO | WO 01/29058 | 4/2001 | |
| WO | WO 01/36646 | 5/2001 | |
| WO | WO 03/008622 | 1/2003 | |
| WO | WO 03/008624 | 1/2003 | |
| WO | WO 03/008642 | 1/2003 | |
| WO | WO03/012066 | 2/2003 | |
| WO | WO 03/066802 | 8/2003 | |
| WO | WO 03/072805 | 9/2003 | |
| WO | WO 03/080645 | 10/2003 | |
| WO | WO 2004/022701 | 3/2004 | |
| WO | WO 2004/067726 | 8/2004 | |
| WO | WO 2004/067764 | 8/2004 | |
| WO | WO 2004/081183 | 9/2004 | |
| WO | WO 2005/026329 | 3/2005 | |
| WO | WO 2005/118853 | 12/2005 | |
| WO | WO2007/028833 | 3/2007 | |
| WO | WO2007/096182 | 8/2007 | |
| WO | WO2007/096702 | 8/2007 | |
| WO | WO2008002920 | * 1/2008 | C12Q 1/68 |
| WO | WO2011/085160 | 7/2011 | |
| WO | WO2015/113828 | 8/2015 | |
| WO | WO2016/004333 | 1/2016 | |

OTHER PUBLICATIONS

McDowell DG, Burns NA, Parkes HC. Localised sequence regions possessing high melting temperatures prevent the amplification of a DNA mimic in competitive PCR. Nucleic Acids Res. Jul. 15, 1998; 26(14):3340-7.*
Allshire, 2002, Science, 297, 1818-1819.
Bass, 2001, Nature, 411, 428-429.
Baulcombe, D., et al, Science 297:2002-03 (2002).
Church et al., Science Apr. 8, 1988:240(4849):185-188.
Corstjens et al., Clinical Chemistry, 47:10, 1885-1893, 2001.
Crain, P. F. and McCloskey, J. A., Current Opinion in Biotechnology 9: 25-34 (1998).
Elbashir et al., 2001, Nature, 411, 494-498.
Hall et al., 2002, Science, 297, 2232-2237.
Hiquchi et al., Nature Biotechnology 10; 413-417, Apr. 1992.
Hutvagner and Zamore, 2002, Science, 297, 2056-60.
Jenuwein, 2002, Science, 297, 2215-2218.
Koster H. et al., Nature Biotechnol., 14: 1123-1128 (1996).
Kurn, N., et al., Clin. Chem. 2005, 51:10, 1973-1981.
Lagos-Quintana, M., et al., Science 294:853-58 (2001).
Lau, N.C., et al, Science 294;858-62 (2001).
Lee, R.C., and Ambros, V., Science 294:862-64 (2001).
Limbach P., MassSpectrom. Rev. 15: 297-336 (1996).
Lizardi, P., et al., Nature Biotech. 1998, 6, 1197-1202.
Llave, C., Science 297:2053-56 (2002).
McManus et al., 2002, RNA, 8, 842-850.
Murray K., J. Mass Spectrom. 31: 1203-1215 (1996).
Notomi, T., et al., NAR 2000, 28, 12, e63.
Reinhart & Bartel, 2002, Science, 297, 1831.
Reinhart et al., 2002, Gene & Dev., 16, 1616-1626.
Ruvkun, GI, Science 294:797-99 (2001).
Tan, E., et al., Anal. Chem. 2005, 77, 7984-7992.
Tyagi et al. Nature Biotechnology 14: Mar. 1996, 303-308.
VanNess, J, et al., PNAS 2003. vol. 100, No. 8, p. 4504-4509.
Volpe et al., 2002, Science, 297, 1833-1837.
Wade, N., "Studies Reveal an Immune System Regulator" New York Times, Apr. 27, 2007.
Zamore at al., 2000, Cell, 101, 25-33.
Cai, "An Inexpensive and Simple Nucleic Acid Dipstick for Rapid Pathogen Detection," LAUR #05-9067 of Los Alamos National Laboratory, Aug. 22, 2006.
Dean et al., "Comprehensive human genome amplification using multiple displacement amplification," Proc. Natl. Acad. Sci. USA, 99(8):5261-66, 2022.
Demidov, "Rolling-circle amplification in DNA diagnostics: the power of simplicity," Expert Rev. Mol. Diagn., 2(6):89-95, 2002.
Saiki et al., "Primer-Directed Enzymatic Amplification of DNA with a Thermostable DNA Polymerase," Science, 239:487-491, 1988.
Singer et al., "Characterization of PicoGreen Reagent and Development of a Fluorescence-Based Solution assay for Double-Stranded DNA Quantitation," Analytical Biochemistry, 249:228-238, 1997.
Office Action in U.S. Appl. No. 12/173,020, mailed Dec. 27, 2010.
Restriction Requirement in U.S. Appl. No. 12/173,020, mailed Sep. 17, 2010.
International Search Report, for the corresponding PCT Application No. PCT/US2008/070023, dated Jan. 19, 2009.
English translation of Chinese Second Office action, for corresponding Chinese application CN 200880105424.7. dated Jun. 5, 2013.
Kentaro Nagimine et al., "Loop-mediated Isothermal Amplification Reaction Using a Nondenatured Template," Clinical Chemistry, 47(9):1742-1743 (2001).

(56) References Cited

OTHER PUBLICATIONS

Extended European Search Report for corresponding EP Application No. 12195331.9-1403 / 2657350, dated Feb. 10, 2013; pp. 1-7.
Extended European Search Report for corresponding EP Application No. 12195333.5-1403, dated Sep. 10, 2013, pp. 1-9.
English translation and Chinese Office action, for corresponding Chinese application CN 200880105424.7. dated Jul. 23, 2012.
AU Office Action for corresponding AU Application No. 2008276118, 4 pages, dated May 1, 2013.
EP Office Action for corresponding EP Application No. 08 781827.4, 8 pages, dated Mar. 13, 2012.
Office Action in U.S. Appl. No. 12/173,020, 24 pages, mailed Mar. 26, 2012.
English translation of Chinese Third Office action, for corresponding Chinese application CN 200880105424.7. dated Feb. 8, 2014.
Notification of the Final Rejection for corresponding Chinese application CN 200880105424.7. dated Jun. 5, 2014.
Sequence of vector pUC19, downloaded from http://genome-www.stanford.edu/vectordb/vector_descrip/COMPLET . . . on Mar. 27, 2014.
Notice of Opposition in corresponding EP Application No. 08781827.4, dated May 6, 2014, pp. 1-36.
Walker et al., "Isothermal in vitro amplification of DNA by a restriction enzyme/DNA polymerase system," PNAS, 89:392-396 (1992).
Notice of Allowance in corresponding Japanese Application No. 2010-517111, dated Jan. 15, 2015, pp. 1-3.
Response to Examination Report in corresponding Australian Application No. 2008276118, dated Jan. 23, 2015, pp. 1-5.
Response to Office Action dated Jul. 31, 2014, for corresponding Canadian Application No. 2693805, dated Jan. 30, 2015, pp. 1-62.
Response of Patentee to Opposition in corresponding EP Application No. 08781827.4 (EP 2 181 196), dated Jan. 7, 2015, pp. 1-36.
Nuovo GJ, "In situ strand displacement amplification: an improved technique for the detection of low copy nucleic acids," Diagnostic Molecular Pathology, 2000, 9(4):195-202.
Zhu et al., "Engineering strand-specific DNA nicking enzymes from the type IIS restriction endonucleases Bsa1, BsmB1, and BsmA1," J. Mol. Biol. 2004, 337:573-583.
Notice of Opposition in corresponding Application No. 08781827.4/2181196, dated Aug. 7, 2015, pp. 1-21.
Walker et al., "Strand displacement amplification—an iso-thermal, in vitro DNA amplification technique," Nucl. Acids Res. 20:1691-1696 (1992).
Walker et al., "Multiplex strand displacement amplification (SDA) and detection of DNA sequences from *Mycobacterium tuberculosis* and other mycobacteria," Nucl. Acids Res. 22:2670-2677 (1994).
Walker, "Empirical Aspects of Strand Displacement Amplification," PCR Methods and Appl., 3:1-6 (1993).
Walker, et al., "Strand displacement amplification as an in vitro model for rolling-circle replication: Deletion formation and evolution during serial transfer," PNAS, 91:7937-7941 (1994).
Extended European Search Report in corresponding Application No. 13799829.0, dated Mar. 31, 2016, pp. 1-10.
Arena et al., "Calcium- and Magnesium-EDTA Complexes. Stability Constants and Their Dependence on Temperature and Ionic Strength," Thermochimica Acta, 61 (1983) 129-138.
Examiner's Report in corresponding Canadian Application No. 2,693,805 dated Mar. 18, 2016, pp. 1-5.
Summons to Oral Proceedings in corresponding European Application No. 08781827.4, dated Jan. 14, 2016, pp. 1-17.
Little et al., "Molecular Diagnostics and Genetics," Clinical Chemistry, 45:6, 777-784 (1999).
Wang et al., "Homogeneous Real-Time Detection of Single-Nucleotide Polymorphisms by Strand Displacement Amplification on the BD ProbeTec ET System," Clinical Chemistry, 49:10, 1599-1607 (2003).
C.A. Spargo et al., "Detection of M. tuberculosis DNA using Thermophilic Strand Displacement Amplification," Molecular and Cellular Probes (1996) 10, 247-256.
Chinese Office Action in Application No. 201410465144.4, dated Jun. 28, 2016, pp. 1-9.
Notification of Reexamination in Chinese Application No. 200880105424.7, pp. 1-8.
Chinese Office Action in Application No. 201410466581.8, dated Jan. 21, 2016, pp. 1-20.
Chinese Office Action in Application No. 201410465144.4, dated Dec. 1, 2015, pp. 1-7.
Ehses et al., "Optimization and design of oligonucleotide setup for strand displacement amplification," J. Biochem. Biophys. Methods, 63 (2005) 170-186.
Artificial DNA: Methods and Applications (2003), Khudyakov Y.E. & Fields, H.A. (Eds), *Synthetic DNA Used in Amplification Reactions* (pp. 115-159), CRC Press LLC.
Nadezhda V. Zyrina et al., "N.BspD6I DNA nickase strongly stimulates template-independent synthesis of non-palindromic repetitive DNA by Bst DNA polymerase," Biol. Chem. vol. 388, pp. 367-372, Apr. 2007.
Notice of the Third Office Action in corresponding Chinese Application No. 201410465144.4, dated Jan. 9, 2017, pp. 1-5.
Notice of the Second Office Action in corresponding Chinese Application No. 2014104666581.8, dated Dec. 2, 2016, pp. 1-17.

* cited by examiner

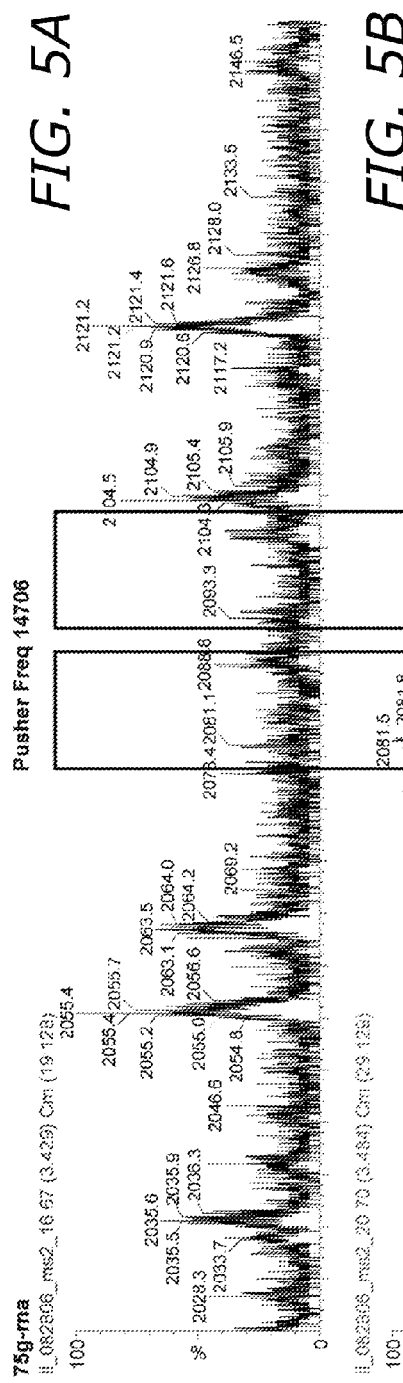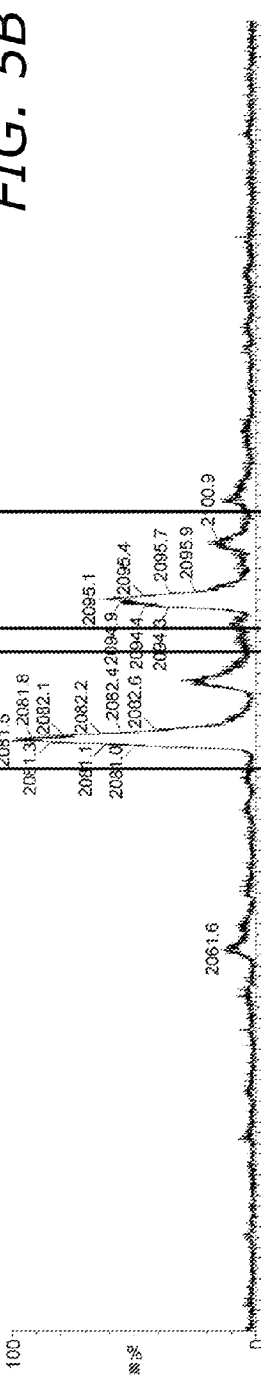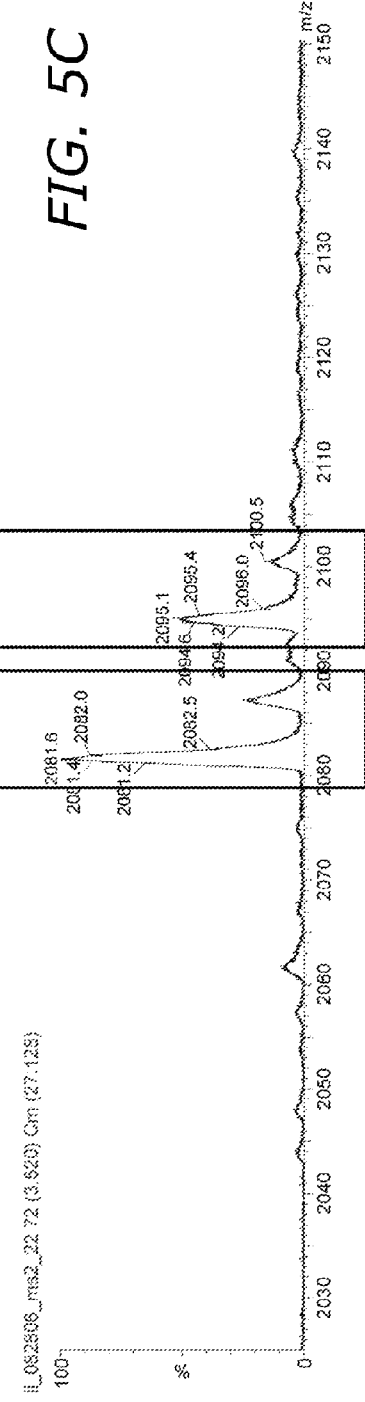
FIG. 5A
FIG. 5B
FIG. 5C

FIG. 18

NICKING AND EXTENSION AMPLIFICATION REACTION FOR THE EXPONENTIAL AMPLIFICATION OF NUCLEIC ACIDS

FIELD OF THE INVENTION

The invention is in general directed to the rapid exponential amplification of short DNA or RNA sequences at a constant temperature.

BACKGROUND

The field of in vitro diagnostics is quickly expanding as the need for systems that can rapidly detect the presence of harmful species or determine the genetic sequence of a region of interest is increasing exponentially. Current molecular diagnostics focus on the detection of biomarkers and include small molecule detection, immuno-based assays, and nucleic acid tests. The built-in specificity between two complementary nucleic acid strands allows for fast and specific recognition using unique DNA or RNA sequences, the simplicity of which makes a nucleic acid test an attractive prospect. Identification of bacterial and viral threat agents, genetically modified food products, and single nucleotide polymorphisms for disease management are only a few areas where the advancement of these molecular diagnostic tools becomes extremely advantageous. To meet these growing needs, nucleic acid amplification technologies have been developed and tailored to these needs of specificity and sensitivity.

Historically, the most common amplification technique is the polymerase chain reaction (PCR), which has in many cases become the gold standard for detection methods because of its reliability and specificity. This technique requires the cycling of temperatures to proceed through the steps of denaturation of the dsDNA, annealing of short oligonucleotide primers, and extension of the primer along the template by a thermostable polymerase. Though many new advances in engineering have successfully shortened these reaction times to 20-30 minutes, there is still a steep power requirement to meet the needs of these thermocycling units.

Various isothermal amplification techniques have been developed to circumvent the need for temperature cycling. From this demand, both DNA and RNA isothermal amplification technologies have emerged.

Transcription-Mediated Amplification (TMA) employs a reverse transcriptase with RNase activity, an RNA polymerase, and primers with a promoter sequence at the 5' end. The reverse transcriptase synthesizes cDNA from the primer, degrades the RNA target, and synthesizes the second strand after the reverse primer binds. RNA polymerase then binds to the promoter region of the dsDNA and transcribes new RNA transcripts which can serve as templates for further reverse transcription. The reaction can produce a billion fold amplification in 20-30 minutes. This system is not as robust as other DNA amplification techniques and is therefore, not a field-deployable test due to the ubiquitous presence of RNAases outside of a sterile laboratory. This amplification technique is very similar to Self-Sustained Sequence Replication (3SR) and Nucleic Acid Sequence Based Amplification (NASBA), but varies in the enzymes employed.

Single Primer Isothermal Amplification (SPIA) also involves multiple polymerases and RNaseH. First, a reverse transcriptase extends a chimeric primer along an RNA target. RNaseH degrades the RNA target and allows a DNA polymerase to synthesize the second strand of cDNA. RNaseH then degrades a portion of the chimeric primer to release a portion of the cDNA and open a binding site for the next chimeric primer to bind and the amplification process proceeds through the cycle again. The linear amplification system can amplify very low levels of RNA target in roughly 3.5 hrs.

The Q-Beta replicase system is a probe amplification method. A probe region complementary to the target of choice is inserted into MDV-1 RNA, a naturally occurring template for Q-Beta replicase. Q-Beta replicates the MDV-1 plasmid so that the synthesized product is itself a template for Q-Beta replicase, resulting in exponential amplification as long as the there is excess replicase to template. Because the Q-Beta replication process is so sensitive and can amplify whether the target is present or not, multiple wash steps are required to purge the sample of non-specifically bound replication plasmids. The exponential amplification takes approximately 30 minutes; however, the total time including all wash steps is approximately 4 hours.

Numerous isothermal DNA amplification technologies have been developed as well. Rolling circle amplification (RCA) was developed based on the natural replication of plasmids and viruses. A primer extends along a circular template resulting in the synthesis of a single-stranded tandem repeat. Capture, washing, and ligation steps are necessary to preferentially circularize the template in the presence of target and reduce background amplification. Ramification amplification (RAM) adds cascading primers for additional geometric amplification. This technique involves amplification of non-specifically sized strands that are either double or single-stranded.

Helicase-dependent amplification (HDA) takes advantage of a thermostable helicase (Tte-UvrD) to unwind dsDNA to create single-strands that are then available for hybridization and extension of primers by polymerase. The thermostable HDA method does not require the accessory proteins that the non-thermostable HDA requires. The reaction can be performed at a single temperature, though an initial heat denaturation to bind the primers generates more product. Reaction times are reported to be over 1 hour to amplify products 70-120 base pairs in length.

Loop mediated amplification (LAMP) is a sensitive and specific isothermal amplification method that employs a thermostable polymerase with strand displacement capabilities and four or more primers. The primers are designed to anneal consecutively along the target in the forward and reverse direction. Extension of the outer primers displaces the extended inner primers to release single strands. Each primer is designed to have hairpin ends that, once displaced, snap into a hairpin to facilitate self-priming and further polymerase extension. Additional loop primers can decrease the amplification time, but complicates the reaction mixture. Overall, LAMP is a difficult amplification method to multiplex, that is, to amplify more than one target sequence at a time, although it is reported to be extremely specific due to the multiple primers that must anneal to the target to further the amplification process. Though the reaction proceeds under isothermal conditions, an initial heat denaturation step is required for double-stranded targets. Amplification proceeds in 25 to 50 minutes and yields a ladder pattern of various length products.

Strand displacement amplification (SDA) was developed by Walker et. al. in 1992. This amplification method uses two sets of primers, a strand displacing polymerase, and a restriction endonuclease. The bumper primers serve to displace the initially extended primers to create a single-strand for the next primer to bind. A restriction site is present in the 5' region of the primer. Thiol-modified nucleotides are incorporated into the synthesized products to inhibit cleavage of the synthesized strand. This modification creates a nick site on the primer side of the strand, which the polymerase can extend. This approach requires an initial heat denaturation step for double-stranded targets. The reaction is then run at a temperature below the melting temperature of the double-stranded target region. Products 60 to 100 bases in length are usually amplified in 30-45 minutes using this method.

These and other amplification methods are discussed in, for example, VanNess, J, et al., PNAS 2003. vol 100, no 8, p 4504-4509; Tan, E., et al., Anal. Chem. 2005, 77, 7984-7992; Lizard, P., et al., Nature Biotech. 1998, 6, 1197-1202; Notomi, T., et al., NAR 2000, 28, 12, e63; and Kurn, N., et al., Clin. Chem. 2005, 51:10, 1973-1981. Other references for these general amplification techniques include, for example, U.S. Pat. Nos. 7,112,423; 5,455,166; 5,712,124; 5,744,311; 5,916,779; 5,556,751; 5,733,733; 5,834,202; 5,354,668; 5,591,609; 5,614,389; 5,942,391; and U.S. patent publication numbers US20030082590; US20030138800; US20040058378; and US20060154286.

There is a need for a quicker method of amplification of single-stranded and double-stranded nucleic acid target sequences that can be performed without temperature cycling and that is suitable for shorter target sequences.

SUMMARY

Provided herein are methods of amplifying nucleic acid target sequences that rely on nicking and extension reactions and amplify shorter sequences in a quicker timeframe than traditional amplification reactions, such as, for example, strand displacement amplification reactions. Embodiments of the invention include, for example, reactions that use only two templates to prime, one or two nicking enzymes, and a polymerase, under isothermal conditions. In exemplary embodiments, the polymerase and the nicking enzyme are thermophilic, and the reaction temperature is significantly above the melting temperature of the hybridized target region. The nicking enzyme nicks only one strand in a double-stranded duplex, so that incorporation of modified nucleotides is not necessary as it is in strand displacement. An initial heat denaturation step is not required for the methods of the present invention. Due to the simplicity of the reaction, in exemplary embodiments, the reaction is very easy to perform and can amplify 20-30 mer products $10^8$ to $10^{10}$ fold from genomic DNA in 2.5 to 10 minutes. Furthermore, in other exemplary embodiments, the method is able to amplify RNA without a separate reverse transcription step.

Thus, provided in a first embodiment of the present invention is a method for amplifying a double-stranded nucleic acid target sequence, comprising contacting a target DNA molecule comprising a double-stranded target sequence having a sense strand and an antisense strand, with a forward template and a reverse template, wherein said forward template comprises a nucleic acid sequence comprising a recognition region at the 3' end that is complementary to the 3' end of the target sequence antisense strand; a nicking enzyme site upstream of said recognition region, and a stabilizing region upstream of said nicking enzyme site; said reverse template comprises a nucleotide sequence comprising a recognition region at the 3' end that is complementary to the 3' end of the target sequence sense strand, a nicking enzyme site upstream of said recognition region, and a stabilizing region upstream of said nicking enzyme site; providing a first nicking enzyme that is capable of nicking at the nicking enzyme site of said forward template, and does not nick within said target sequence; providing a second nicking enzyme that is capable of nicking at the nicking enzyme site of said reverse template and does not nick within said target sequence; and providing a DNA polymerase; under conditions wherein amplification is performed by multiple cycles of said polymerase extending said forward and reverse templates along said target sequence producing a double-stranded nicking enzyme site, and said nicking enzymes nicking at said nicking enzyme sites, producing an amplification product.

In certain embodiments of the invention, the DNA polymerase is a thermophilic polymerase. In other examples of the invention, the polymerase and said nicking enzymes are stable at temperatures up to 37° C., 42° C., 60° C., 65° C., 70° C., 75° C., 80° C., or 85° C. In certain embodiments, the polymerase is stable up to 60° C. The polymerase may, for example, be selected from the group consisting of Bst (large fragment), 9° N, Vent$_R$® (exo-) DNA Polymerase, THERMINATOR, and THERMINATOR II.

The nicking enzyme may, for example, nick upstream of the nicking enzyme binding site, or, in exemplary embodiments, the nicking enzyme may nick downstream of the nicking enzyme binding site. In certain embodiments, the forward and reverse templates comprise nicking enzyme sites recognized by the same nicking enzyme and said first and said second nicking enzyme are the same. The nicking enzyme may, for example, be selected from the group consisting of Nt.BspQI, Nb.BbvCi, Nb.BsmI, Nb.BsrDI, Nb.BtsI, Nt.AlwI, Nt.BbvCI, Nt.BstNBI, Nt.CviPII, Nb.Bpu10I, and Nt.Bpu10I.

In certain aspects of the present invention, the target sequence comprises from 1 to 5 nucleotides more than the sum of the nucleotides of said forward template recognition region and said reverse template recognition region.

The DNA molecule may be, for example, genomic DNA. The DNA molecule may be, for example, selected from the group consisting of plasmid, mitochondrial, and viral DNA. In certain embodiments, the forward template is provided at the same concentration as the reverse template. In other examples, the forward template is provided at a ratio to the reverse template at the range of ratios of 1:100 to 100:1.

In other examples of the invention, the method further comprises the use of a second polymerase. The amplification may be, for example, conducted at a constant temperature. This temperature may be, for example, between 54° C. and 60° C. As to the length of time for the reaction to take place, in certain examples, the amplification reaction is held at constant temperature for 1 to 10 minutes.

The present invention further comprises detecting the amplification product, for example, by a method selected from the group consisting of gel electrophoresis, mass spectrometry, SYBR I fluorescence, SYBR II fluorescence, SYBR Gold, PICOGREEN, TOTO-3, intercalating dye detection, FRET, molecular beacon detection, surface capture, capillary electrophoresis, incorporation of labeled nucleotides to allow detection by capture, fluorescence polarization, and lateral flow capture. The amplification products may be, for example, detected using a solid surface method, for example, where at least one capture probe is immobilized on the solid surface that binds to the amplified sequence.

The present invention may be used for multiplex amplification. Thus, for example, in certain embodiments of the present invention at least two target sequences are capable of being amplified. By "capable of being amplified" is meant the amplification reaction comprises the appropriate templates and enzymes to amplify at least two target sequences. Thus, for example, the amplification reaction may be prepared to detect at least two target sequences, but only one of the target sequences may actually be present in the sample being tested, such that both sequences are capable of being amplified, but only one sequence is. Or, where two target sequences are present, the amplification reaction may result in the amplification of both of the target sequences. The multiplex amplification reaction may result in the amplification of one, some, or all, of the target sequences for which it comprises the appropriate templates and enzymes.

At least one of the templates, for example, may comprise a spacer, a blocking group, or a modified nucleotide.

Also provided as an embodiment of the present invention is a method for amplifying a single-stranded nucleic acid target sequence, comprising contacting a target nucleic acid comprising a single-stranded target sequence with a reverse template, wherein said reverse template comprises a nucleotide sequence comprising a recognition region at the 3' end that is complementary to the 3' end of the target sequence, a nicking enzyme site upstream of said recognition region, and a stabilizing region upstream of said nicking enzyme site; providing a first nicking enzyme that is capable of nicking at the nicking enzyme site of said reverse template, and does not nick within said target sequence; providing a DNA polymerase under conditions wherein said polymerase extends said reverse template along said target sequence; contacting said extended reverse template with a forward template, wherein said forward template comprises comprising a recognition region at the 3' end that is identical to the 5' end of the target sequence a nicking enzyme site upstream of said recognition region, and a stabilizing region upstream of said nicking enzyme site; providing a second nicking enzyme that is capable of nicking at the nicking enzyme site of said forward template and does not nick within said target sequence; under conditions wherein amplification is performed by multiple cycles of said polymerase extending said forward and reverse templates along said target sequence producing a double-stranded nicking enzyme site, and said nicking enzymes nicking at said nicking enzyme sites, producing an amplification product.

Those of ordinary skill in the art understand that the examples presented herein relating to the amplification of a double-stranded nucleic acid target sequence and the detection of the amplified product also apply to the amplification of a single-stranded nucleic acid target sequence and the detection of the amplified product. Further, in examples of the present invention, the target sequence may be, for example, RNA, for example, but not limited to, messenger RNA, viral RNA, microRNA, a microRNA precursor, or siRNA. In exemplary embodiments of the present invention, the polymerase comprises reverse transcription activity. In yet other examples of the present invention, the target sequence is DNA, such as, for example, genomic DNA, or for example, the target sequence is selected from the group consisting of plasmid, mitochondrial, and viral nucleic acid.

Where the method may comprise the use of more than one polymerase, in exemplary embodiments at least one of the polymerases comprises reverse transcriptase activity.

In other embodiments of the present invention, a set of oligonucleotide templates is provided, comprising a first template for nucleic acid amplification, comprising a recognition region at the 3' end that is complementary to the 3' end of a target sequence antisense strand; a nicking enzyme site upstream of said recognition region; and a stabilizing region upstream of said nicking enzyme site; and a second template for nucleic acid amplification, comprising a recognition region at the 3' end that is identical to the 5' of said target sequence antisense strand; a nicking enzyme site upstream of said recognition region; and a stabilizing region upstream of said nicking enzyme site;

wherein said target sequence comprises from 1 to 5 spacer bases between said 3' end of the antisense strand and said 5' end of said antisense strand that do not bind to either template.

In yet other embodiments, a kit is provided for following the methods of the present invention for nucleic acid amplification, comprising a DNA polymerase; a first template for nucleic acid amplification, comprising a recognition region at the 3' end that is complementary to the 3' end of a target sequence antisense strand; a nicking enzyme site upstream of said recognition region; and a stabilizing region upstream of said nicking enzyme site; a second template for nucleic acid amplification, comprising a recognition region at the 3' end that is complementary to the 3' end of a target sequence sense strand; a nicking enzyme site upstream of said recognition region; and a stabilizing region upstream of said nicking enzyme site; one or two thermostable nicking enzymes, wherein either one enzyme is capable of nicking at the nicking enzyme site of said first and said second templates, or a first enzyme is capable of nicking at the nicking enzyme site of said first primer and a second enzyme is capable of nicking at the enzyme site of said second primer.

The kit may, for example, provide said polymerase, nicking enzymes, and templates in a container. The kit may provide, for example, said polymerase, nicking enzymes, and templates in two containers. In certain examples, the polymerase and nicking enzymes are in a first container, and said templates are in a second container. In certain examples, the polymerase and nicking enzymes are lyophilized. The kit may, for example, further comprise instructions for following the amplification methods of the present invention. The kit may, for example, further comprise a cuvette. The kit may, for example, further comprise a lateral flow device or dipstick. The lateral flow device or dipstick may, for example, further comprise a capture probe, wherein said capture probe binds to amplified product. The kit may, for example, further comprise a detector component selected from the group consisting of a fluorescent dye, colloidal gold particles, latex particles, a molecular beacon, and polystyrene beads. In other examples, at least one of the templates of the kit comprises a spacer, blocking group, or a modified nucleotide.

Deoxynucleoside triphosphates (dNTPs) are included in the amplification reaction. One or more of the dNTPs may be modified, or labeled, as discussed herein. Nucleotides are designated as follows. A ribonucleoside triphosphate is referred to as NTP or rNTP; N can be A, G, C, U or m5U to denote specific ribonucleotides. Deoxynucleoside triphosphate substrates are indicated as dNTPs, where N can be A, G, C, T, or U. Throughout the text, monomeric nucleotide subunits may be denoted as A, G, C, or T with no particular reference to DNA or RNA.

In another embodiment, a method is provided for nucleic acid amplification comprising forming a mixture of a target nucleic acid comprising a double-stranded target sequence having a sense strand and an antisense strand; a forward template comprising a nucleic acid sequence comprising a recognition region at the 3' end that is complementary to the 3' end of the target sequence antisense strand; a nicking enzyme site upstream of said recognition region, and a stabilizing region upstream of said nicking enzyme site; a reverse template comprising a nucleotide sequence comprising a recognition region at the 3' end that is complementary to the 3' end of the target sequence sense strand, a nicking enzyme site upstream of said recognition region and a stabilizing region upstream of said nicking enzyme site; a first nicking enzyme that is capable of nicking at the nicking enzyme site of said forward template, and does not nick within said target sequence; a second nicking enzyme that is capable of nicking at the nicking enzyme site of said reverse template and does not nick within said target sequence; and a thermophilic polymerase under conditions wherein amplification is performed by multiple cycles of said polymerase extending said forward and reverse templates along said target sequence producing a double-stranded nicking enzyme site, and said nicking enzymes nicking at said nicking enzyme sites, producing an amplification product. In certain embodiments, the nicking enzyme sites on the forward and reverse templates are recognized by the same nicking enzyme, and only one nicking enzyme is used for the reaction.

In another embodiment, a method is provided for nucleic acid amplification comprising forming a mixture of a target nucleic acid comprising a single-stranded target sequence; a reverse template, wherein said reverse template comprises a nucleotide sequence comprising a recognition region at the 3' end that is complementary to the 3' end of the target sequence, a nicking enzyme site upstream of said recognition region, and a stabilizing region upstream of said nicking enzyme site; a first nicking enzyme that is capable of nicking at the nicking enzyme site of said reverse template, and does not nick within said target sequence; a thermophilic polymerase under conditions wherein said polymerase extends said reverse template along said target sequence; a forward template, wherein said forward template comprises a nucleic acid sequence comprising a recognition region at the 3' end that is identical to the 5' end of the target sequence; and a second nicking enzyme that is capable of nicking at the nicking enzyme site of said forward template and does not nick within said target sequence; under conditions wherein amplification is performed by multiple cycles of said polymerase extending said forward and reverse templates along said target sequence producing a double-stranded nicking enzyme site, and said nicking enzymes nicking at said nicking enzyme sites, producing an amplification product. In certain embodiments, the nicking enzyme sites on the forward and reverse templates are recognized by the same nicking enzyme, and only one nicking enzyme is used for the reaction.

In other embodiments of the invention are provided methods for the separation of amplified nucleic acids obtained by the amplification methods of the invention. In yet further embodiments of the invention are provided methods for detecting and/or analyzing the amplified nucleic acids obtained by the amplification methods of the invention, including, for example, methods using SYBR I, II, SYBR Gold, PICOGREEN, TOTO-3, and most intercalating dyes, molecular beacons, FRET, surface capture using immobilized probes with fluorescence, electrochemical, or colorimetric detection, mass spectrometry, capillary electrophoresis, the incorporation of labeled nucleotides to allow detection by capture or fluorescence polarization, lateral flow, and other methods involving capture probes. Methods using capture probes for detection include, for example, the use of a nucleic acid molecule (the capture probe) comprising a sequence that is complementary to the amplified product such that the capture probe binds to amplified nucleic acid. The reaction may, for example, further comprise an antibody directed against a molecule incorporated into or attached to the capture probe. Or, for example, the capture probe, or a molecule that binds to the capture probe, may incorporate, for example, an enzyme label, for example, peroxidase, alkaline phosphatase, or beta-galactosidase, a fluorescent label, such as, for example, fluorescein or rhodamine, or, for example, other molecules having chemiluminescent or bioluminescent activity. The embodiments of the present invention also comprise combinations of these detection and analysis methods.

BRIEF DESCRIPTION OF THE DRAWINGS

FIG. 1D is a legend for FIG. 1.

The NEAR reaction was run for 2.5 minutes at 56° C., then heat denatured at 94° C. for 4 minutes. Six µL of the reaction was run on a 20% polyacrylamide gel at 160V for ~2.5 hrs. The gel was stained with SYBR II gel stain. Lane 1: NEAR reaction no target control for 25 mer assay. Lane 2: NEAR reaction no target control for 27 mer assay. Lane 3: NEAR reaction for 25 mer assay with 3.5E+5 copies of genomic *Bacillus subtilis* DNA. Lane 4: NEAR reaction for 27 mer assay with 1.1E+6 copies of genomic *Bacillus subtilis* DNA.

Figure 3:
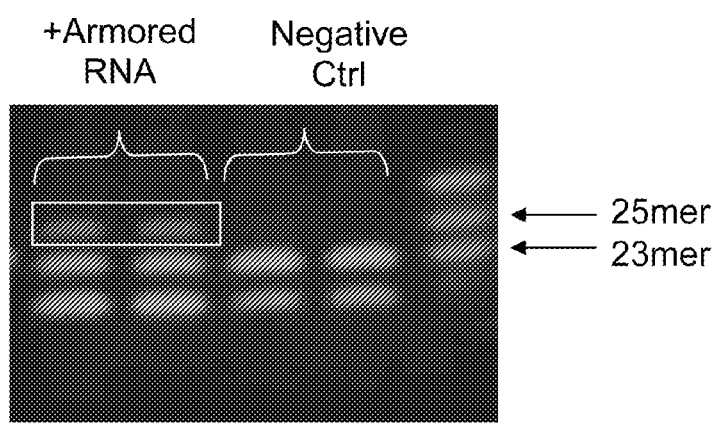

FIG. 3. 20% polyacrylamide gel of reaction products from an RNA NEAR assay.

The NEAR reaction was run for 12 minutes at 56° C., then heat denatured at 94° C. for 4 minutes. Six µL of the reaction was run on a 20% polyacrylamide gel at 160V for ~2.5 hrs. The gel was stained with SYBR II gel stain. Lane 1 & 2: NEAR reaction for 25 mer assay with 1E+6 copies of Ebola Armored RNA (Ambion). Lane 3 & 4: NEAR reaction no target control for 25 mer assay. 25 mer reaction products are outlined in the white box.

Figures 4A, 4B:
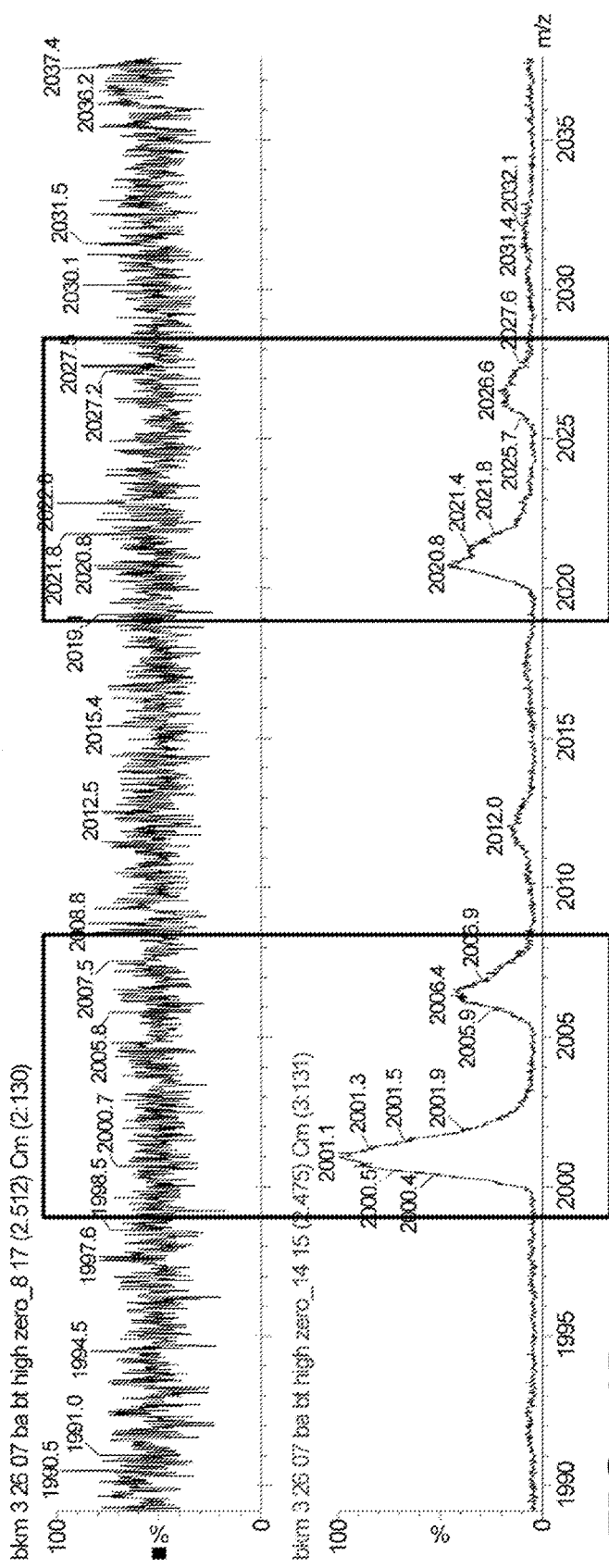

FIG. 4. Mass Spectrum of *Bacillus anthracis* DNA assay products.

A) 0 copies of target or B) 5E+5 copies of genomic DNA added to the NEAR reaction. The NEAR reaction was run for 10 minutes, then heat denatured at 94° C. for 4 minutes. Ten micro liters of sample was injected into the LC/ESI-MS. The (−4) charge state of the 26 mer product and its complementary sequence are outlined in a black box. The smaller adjacent peaks are the sodium adducts of the main product.

FIG. 5. Mass Spectrum of MS2 genomic RNA assay products.

A) 0 copies of target, B) 1E+6 copies of MS2 genomic RNA, or C) 1E+6 copies of synthetic target DNA added to the NEAR reaction. The NEAR reaction was run for 10 minutes, then heat denatured at 94° C. for 4 minutes. Ten micro liters of sample was injected into the LC/ESI-MS. The (−4) charge state of the 27 mer product and its complement sequence are outlined in a black box. The smaller adjacent peaks are the sodium adducts of the main product.

Figure 6:
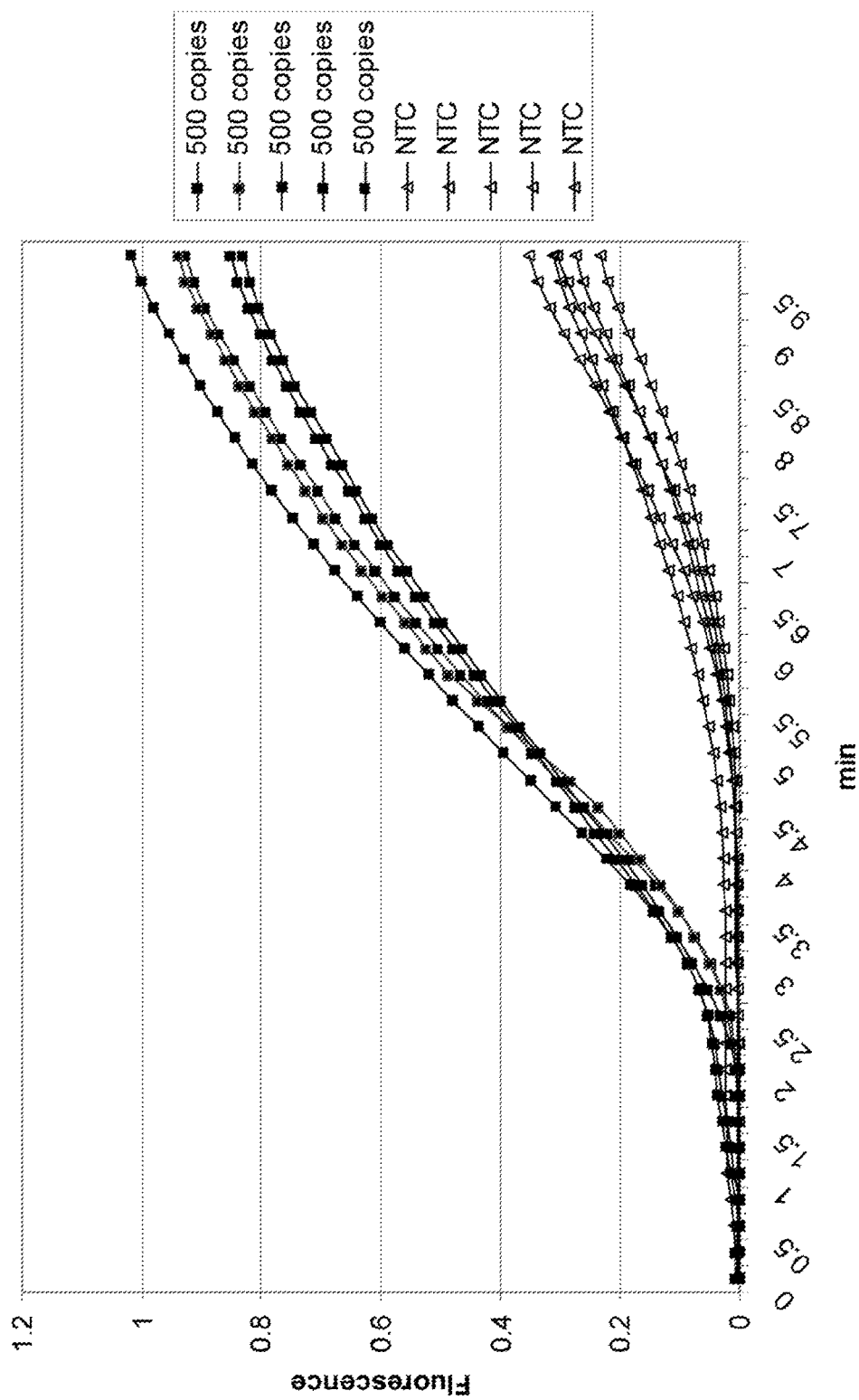

FIG. 6. Real-time detection of NEAR assay amplification using intercalating fluorescent dyes.

Real-time amplification of *Yersinia pestis* genomic DNA at 500 copies (squares) compared to the no target control (NTC, open triangles). The reaction was run for 10 minutes at 58° C. and monitored by the real-time fluorescence with SYBR II (n=5).

Figure 7:
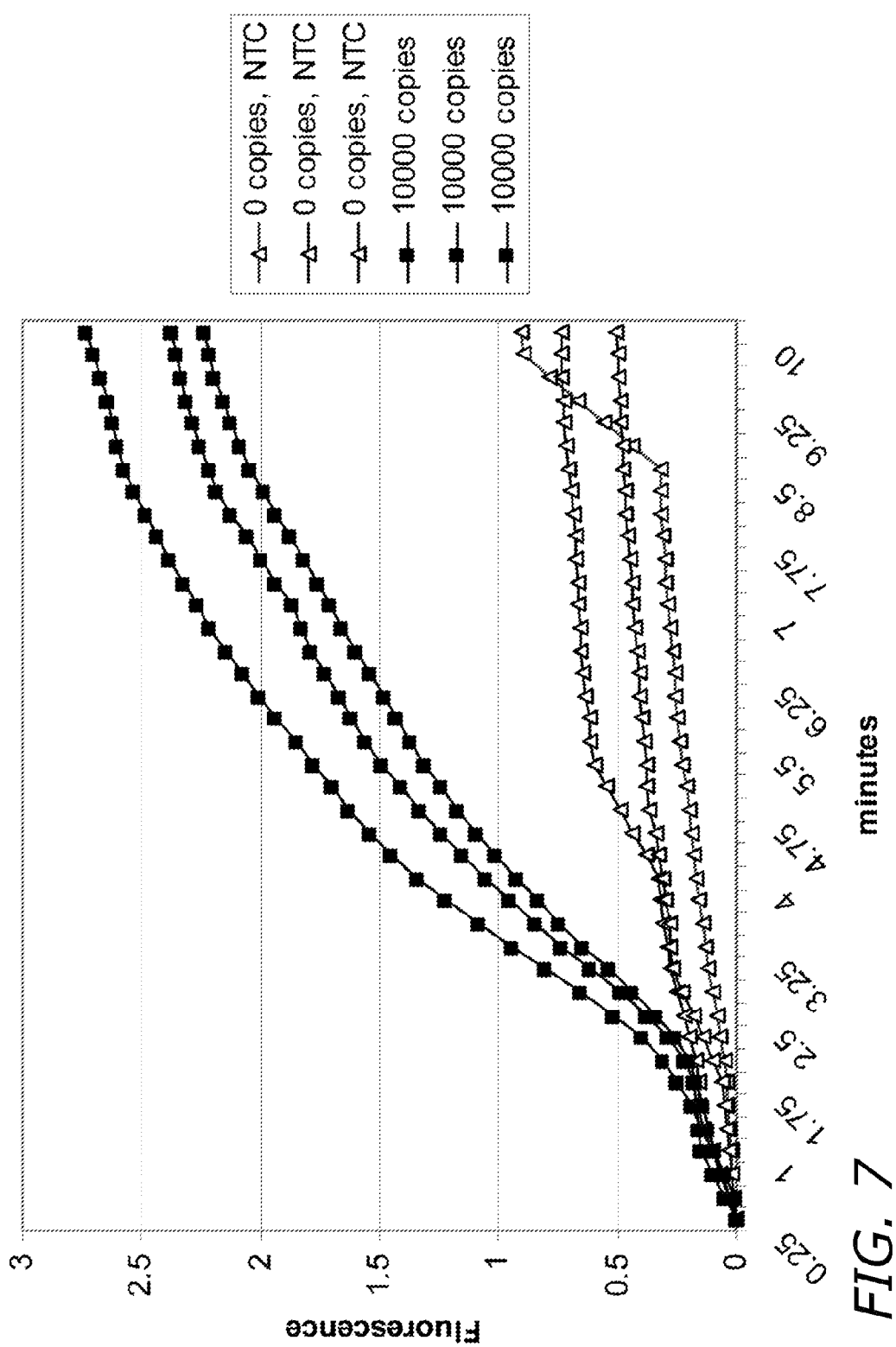

FIG. 7. Real-time detection of NEAR assay amplification using fluorescence resonance energy transfer (FRET).

Real-time amplification of *Yersinia pestis* synthetic DNA at 10,000 copies (squares) compared to the no target control (NTC, open triangles). The reaction was run for 10 minutes at 57° C., n=3.

Figure 8:
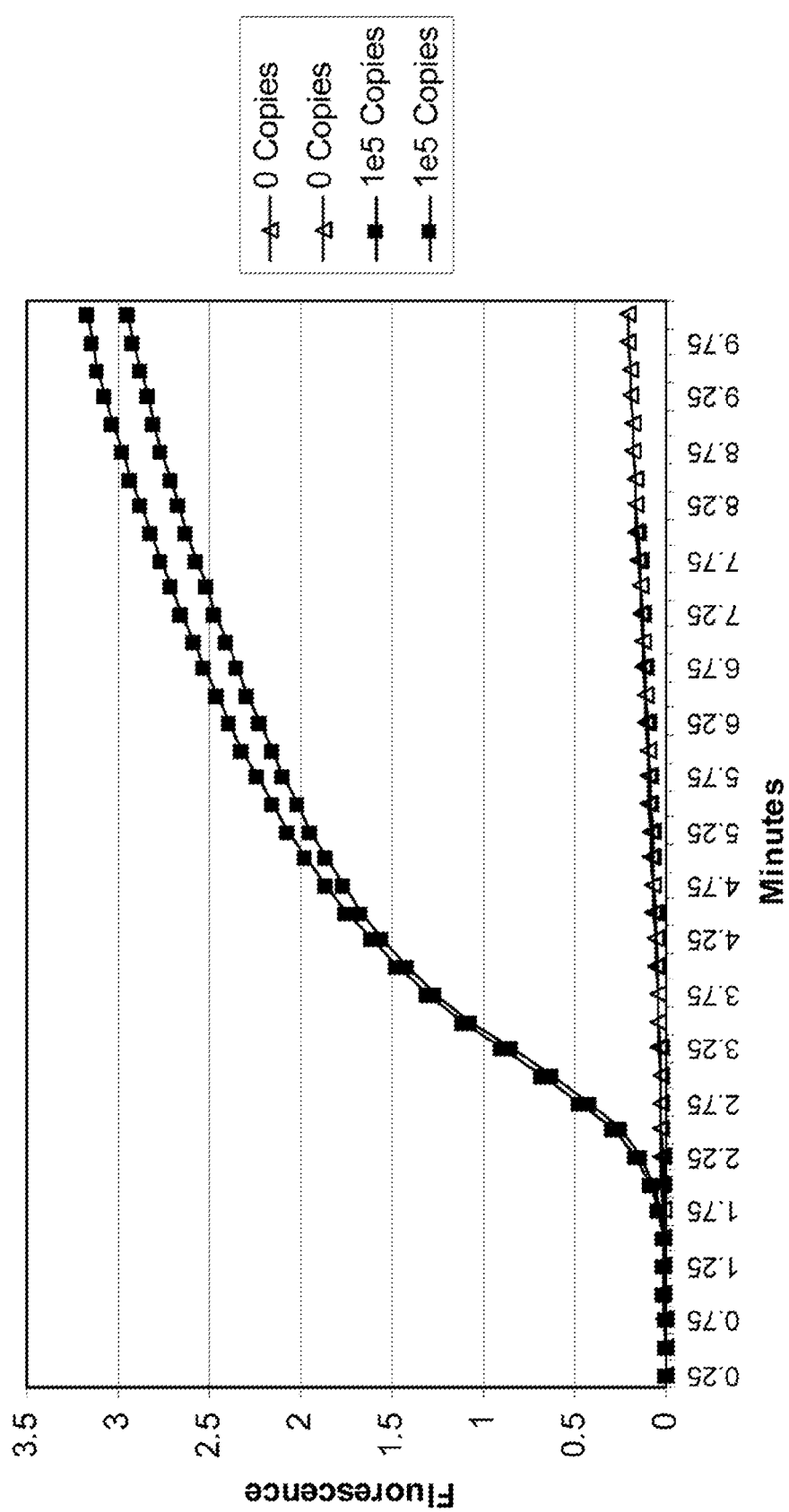

FIG. 8. *Francisella tularensis* assay amplification detected in real-time using molecular beacons.

Either 0 copies (open triangles) or 1E+5 copies (squares) were added to the reaction mix and run for 10 minutes at 57.5° C.

Figure 9:
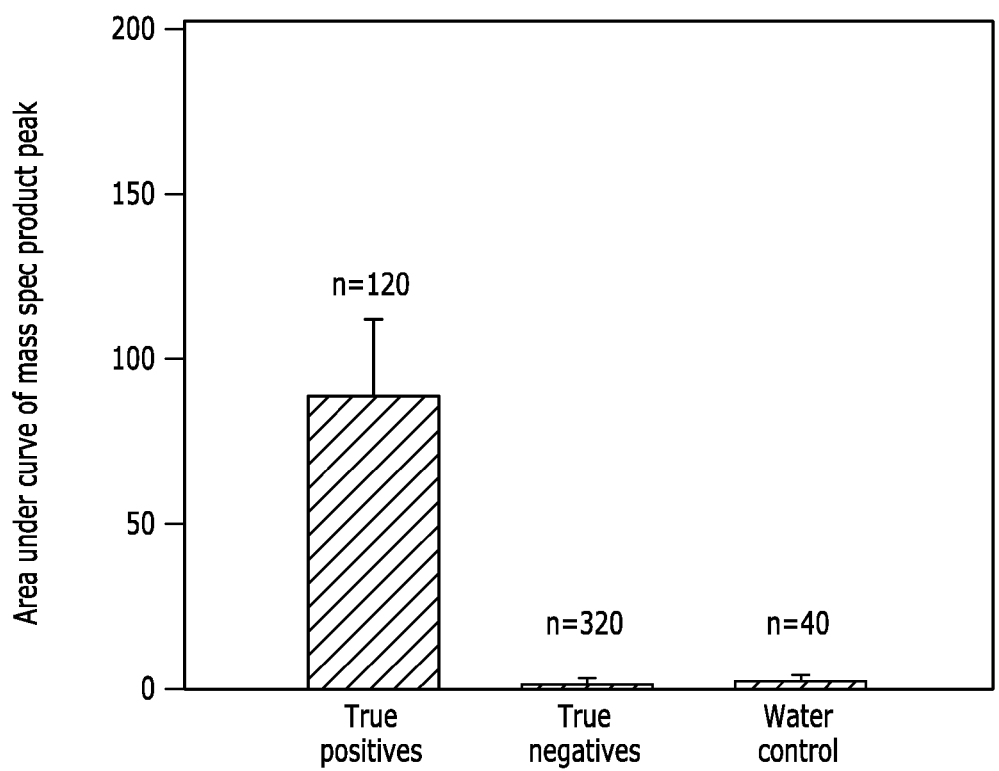

FIG. 9. False alarm rate testing results comparing average AUC values.

Error bars denote one standard deviation. *Bacillus subtilis* NEAR assays were run for 10 min at 55° C. in the presence and absence of *Bacillus subtilis* genomic DNA. Enzymes were heat denatured at 94° C. for 4 min. A 10 μL sample was injected into the LC/ESI-MS and the area under the curve (AUC) of the product peaks were analyzed. True Positives contained 10,000 copies of *Bacillus subtilis* along with 990,000 copies of near neighbor (*Bacillus thuringiensis*). True Negatives contained 10,000 copies of *E. coli* with 990,000 copies of near neighbor, and water negatives contained no DNA as a control.

Figure 10:
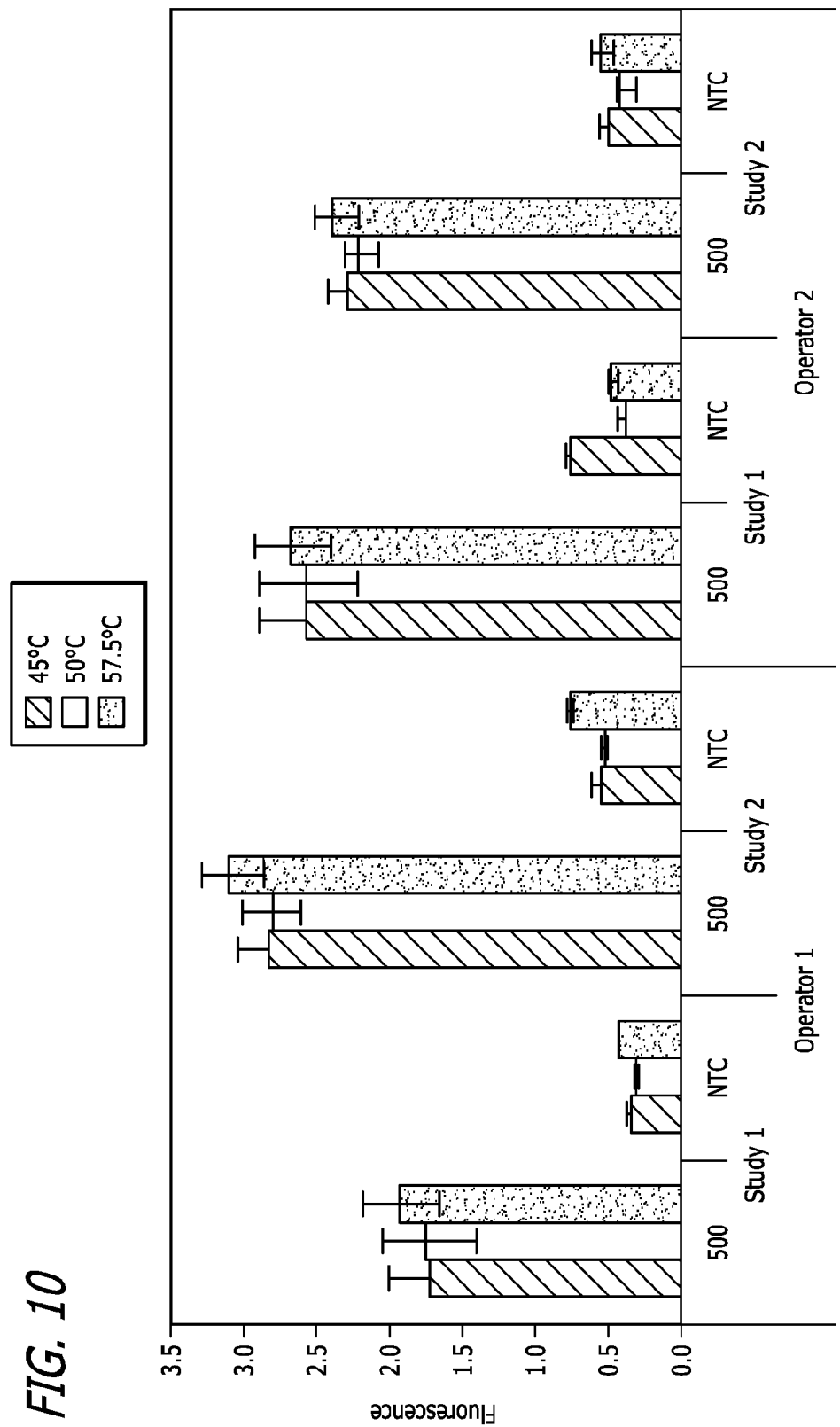

FIG. 10. Replication study of the NEAR Assay using molecular beacon detection with different operators performing the experiments on two different days.

The NEAR reaction was run for 10 minutes at 57.5° C. (in the presence and absence of 500 copies of *Francisella tularensis* genomic DNA) with a 4 min heat kill at 94° C. 300 nM molecular beacon was added and monitored at 45, 50, and 57° C. (n=24).

Figure 11:
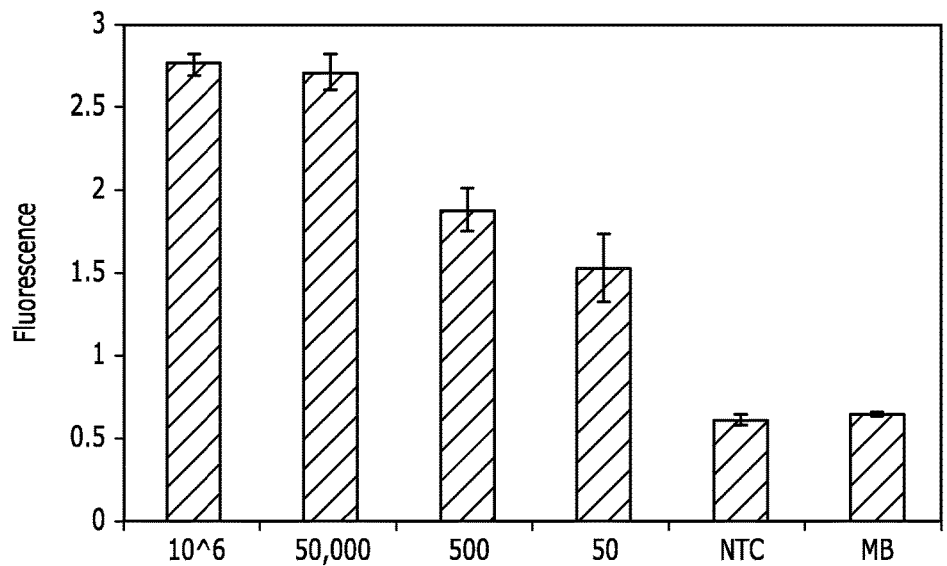

FIG. 11. Sensitivity of the NEAR reaction using molecular beacon detection.

The NEAR assay was run for 10 minutes 57.5° C. The reaction was stopped with a 4 min heat denaturation step at 94° C. 300 nM molecular beacon was added and the fluorescence was monitored at 57.5° C. (n=3). Fluorescence was monitored for beacon opening in the presence NEAR reactions amplified with 1E+6, 5E+5, 5E+4, 5E+2, 50, and 0 (NTC) input copies of *Francisella tularensis* genomic DNA, and compared to the background fluorescence of the beacon alone (MB).

Figure 12:
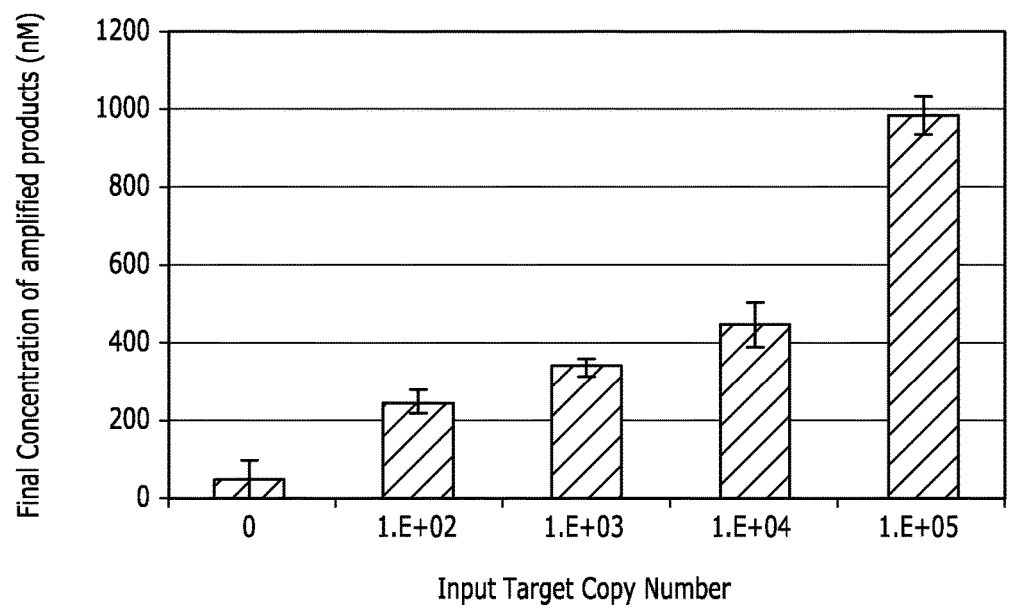

FIG. 12. Final concentration of amplified products in the NEAR reaction.

The NEAR reaction was run for 10 min at 55° C. with varying copies of *Bacillus subtilis* genomic DNA. The reaction was stopped with a heat denaturation step at 94° C. for 4 minutes. A 10 μL sample was injected into the LC/ESI-MS and the AUC of the product peak at 1944 Daltons was analyzed and compared to a standard curve.

Figure 13:
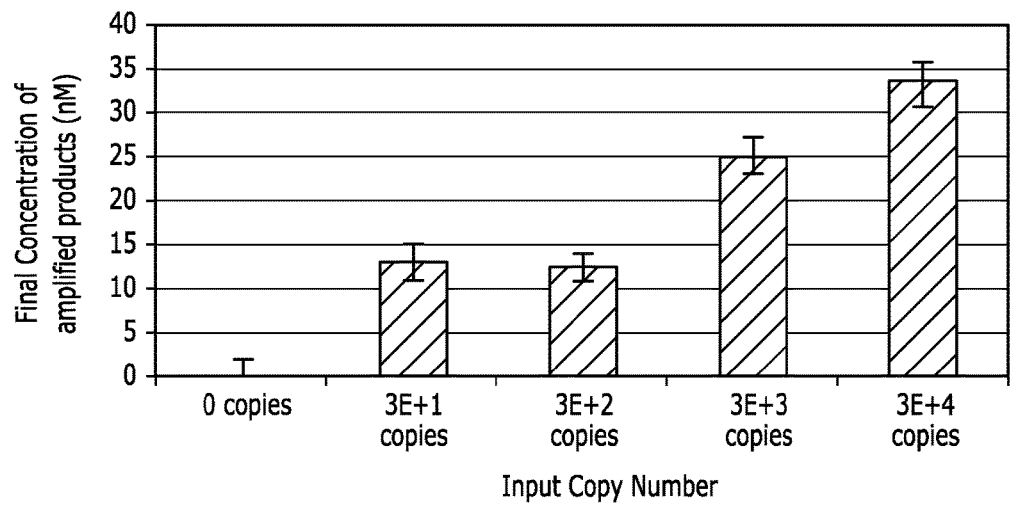

FIG. 13. Correlation of the input RNA target copy number to the final concentration of amplified products.

The Ebola NEAR assay was run for 12 min at 55° C. with varying copies of synthetic RNA corresponding to the Ebola genome DNA. The reaction was stopped with a heat denaturation step at 94° C. for 4 minutes. A 10 μL sample was injected into the LC/ESI-MS and the AUC of the product peak at 1936 Daltons was analyzed and compared to the standard curve of AUC values. (n=3)

Figure 14:
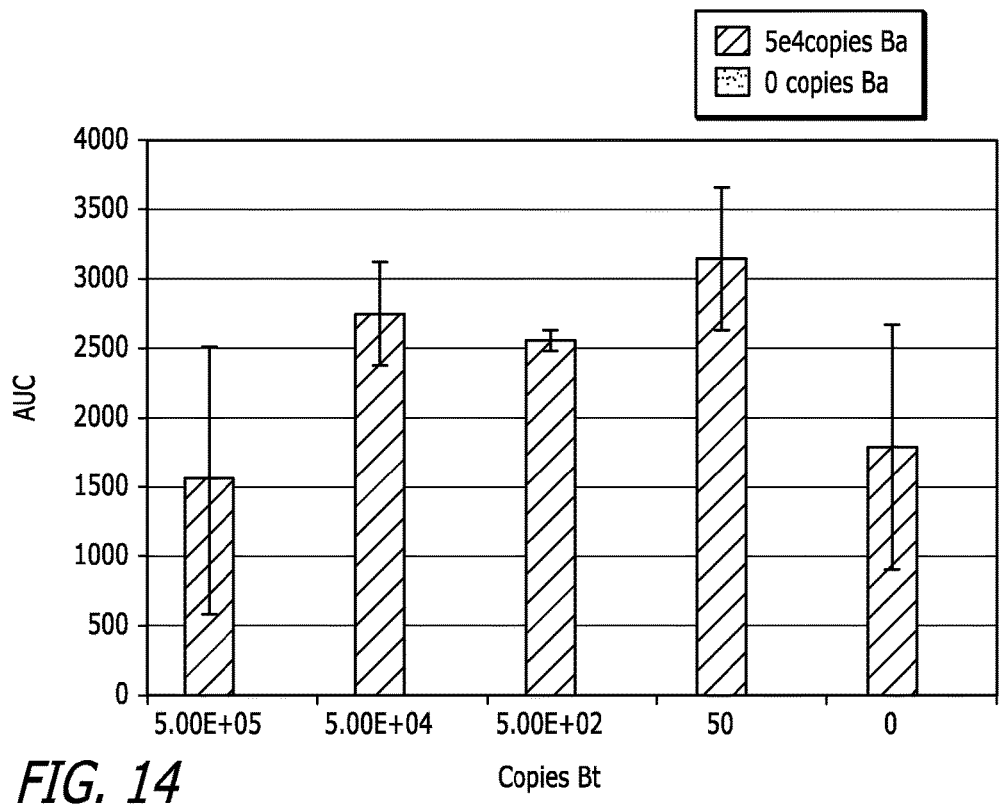

FIG. 14. Mass spec product analysis demonstrating NEAR reaction specificity.

The *Bacillus anthracis* NEAR reaction was run in the presence of a dilution of copies of *Bacillus thuringiensis* for 10 min at 56° C. (n=3), then heat denatured at 94° C. for 4 minutes. A 10 μL sample was injected into the LC/ESI-MS and AUC values of product peaks analyzed.

Figure 15:
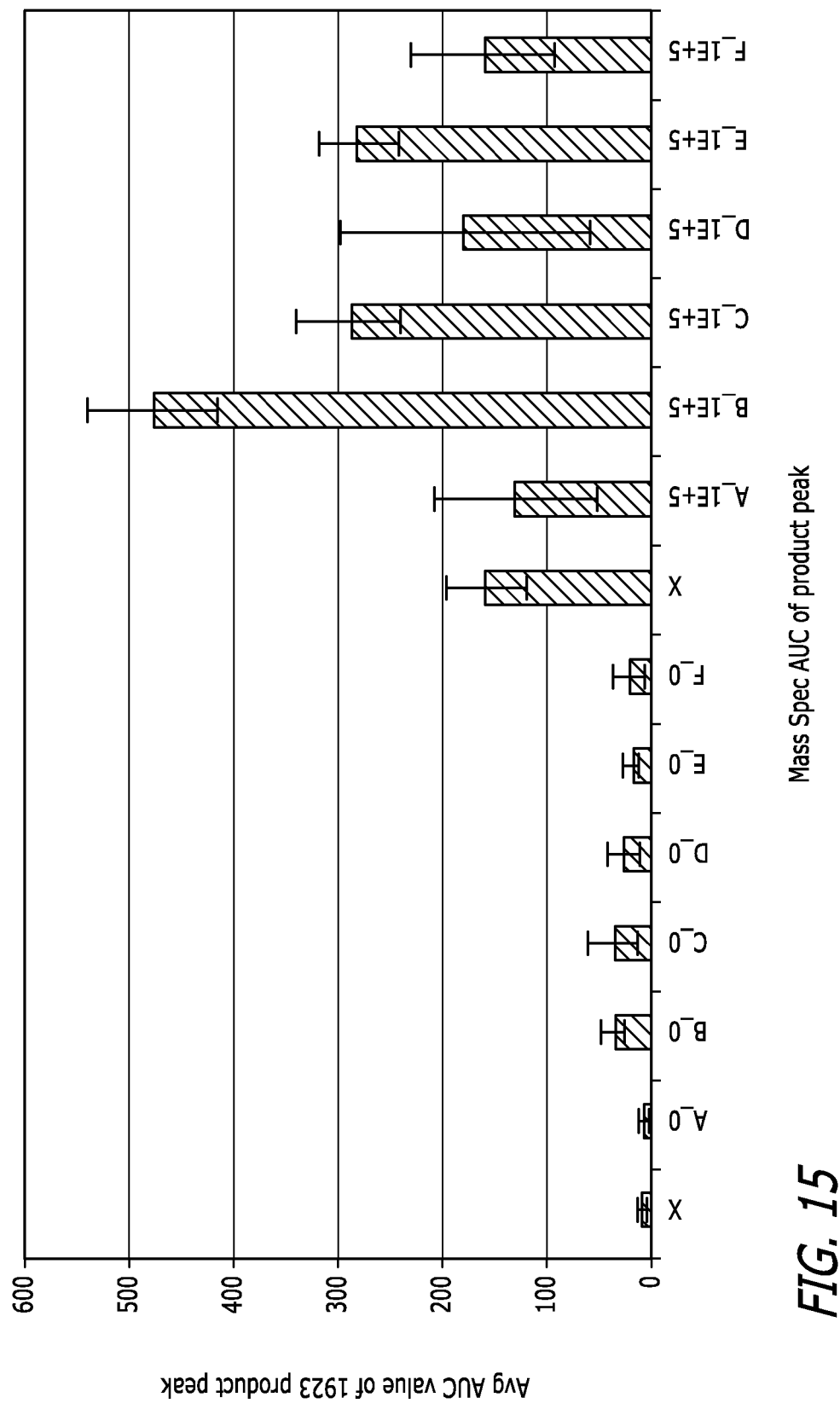

FIG. 15. The effect of an interferent panel on the NEAR amplification.

*Bacillus subtilis* NEAR DNA reactions were run for 10 min at 55° C. and heated to 94° C. for 4 minutes to stop the reaction. Reactions were run in triplicate in the presence 1E+5 copies of *Bacillus subtilis* genomic DNA ("_1E+5") or with no target DNA present ("_0"). Sample x is the control assay with no interferent added. Interferents A through F were added at 50% reaction volume to the *Bacillus subtilis* assay. The AUC of mass spec product peaks were analyzed using a two-way ANOVA and Bonferroni t-test. (Key: A=none; B=House dust, skim milk; C=AZ test dust, humic acid; D=Diesel soot; E=Skim milk; F=Mold spores)

Figure 16:
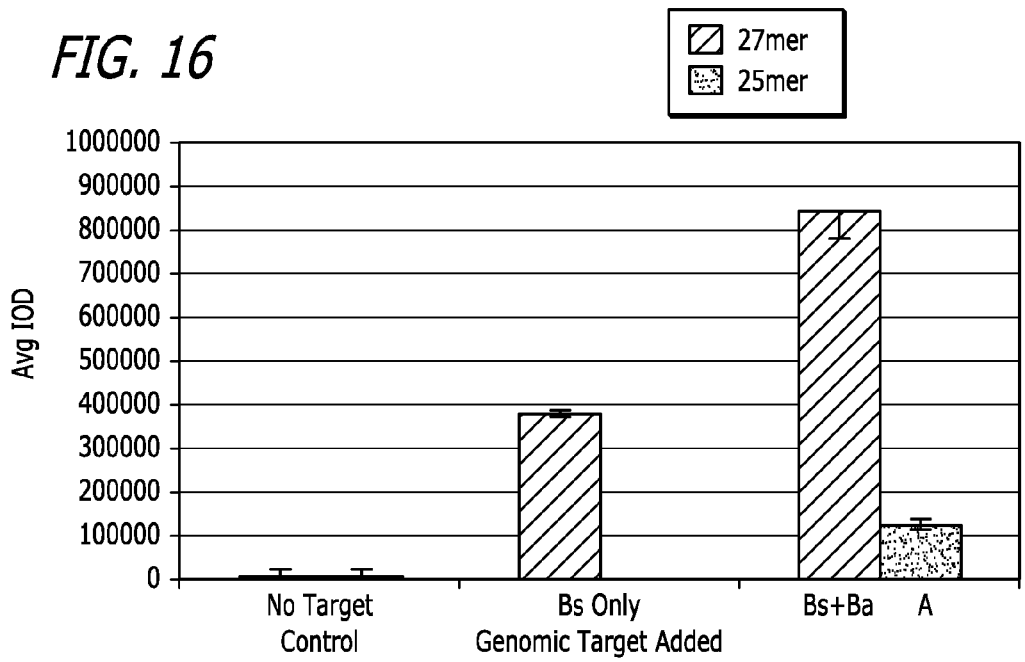

FIG. 16. Gel electrophoresis results for the *Bacillus subtilis*/*Bacillus anthracis* DNA duplex reaction.

The NEAR reaction including templates for both *Bacillus subtilis* (Bs) and *Bacillus anthracis* (Ba) assays was run in the absence of target DNA (negative), in the presence of *Bacillus subtilis* only (positive for 27 mer product), and in the presence of both *Bacillus subtilis* and *Bacillus anthracis* (positive for 27 mer and 25 mer product respectively). The target copy number used in this assay was 500,000 copies. The assay was run for 10 min at 57° C. Templates varied in concentration between the assays to control the amplification (100 nM for *Bacillus anthracis* and 50 nM for *Bacillus subtilis*). Samples were run on a 20% polyacrylamide gel at 160 V for ~2 hours. The gel was stained with SYBR II fluorescent dye and imaged. The fluorescent bands were quantitated and analyzed as the integrated optical density (IOD) (n=8).

Figure 17:
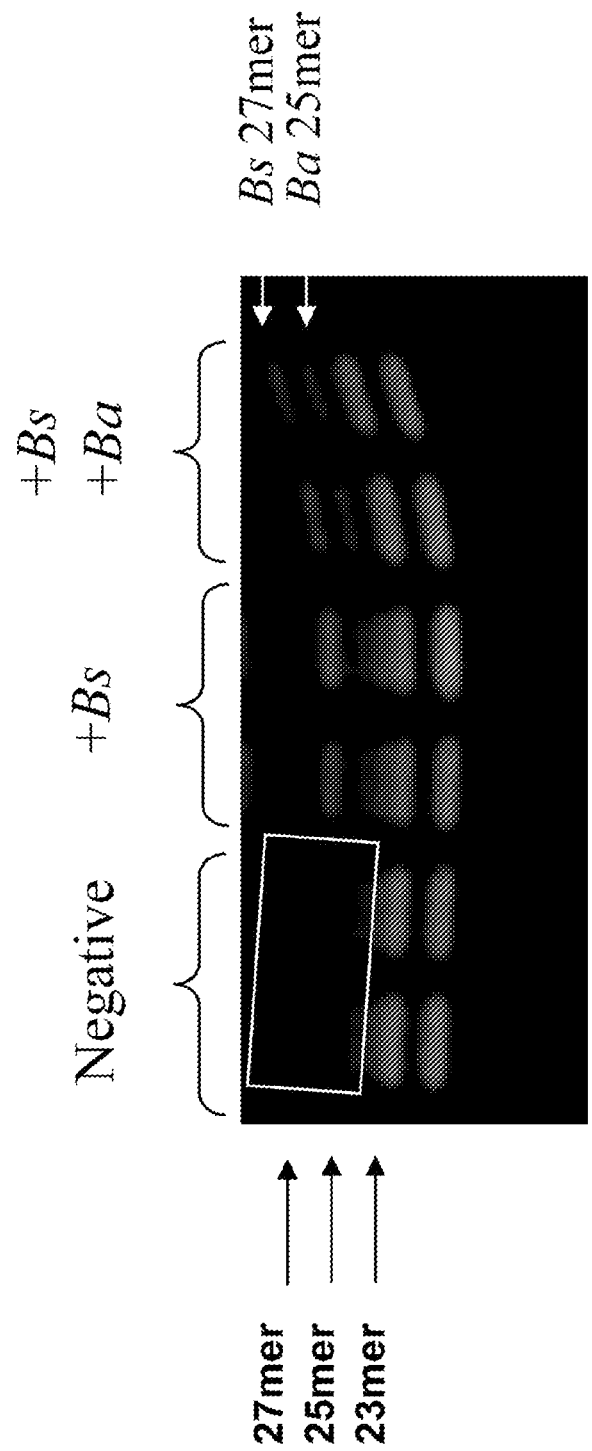

FIG. 17. Specificity results for the *Bacillus subtilis*/ *Bacillus anthracis* DNA duplex reaction shown by gel electrophoresis.

The NEAR reaction including templates for both a *Bacillus subtilis* (Bs) and *Bacillus anthracis* (Ba) assay was run in the absence of target DNA (negative), in the presence of *Bacillus subtilis* only (27 mer product), and in the presence of both *Bacillus subtilis* and *Bacillus anthracis* (27 mer and 25 mer product respectively). The target copy number for each genome present in this assay was 500,000 copies. All reactions contained 500,000 copies of *Bacillus thuringiensis* as clutter. Templates varied in concentration between the assays to control the amplification. The assay was run for 10 min at 57° C., heat denatured at 94° C. for 4 min, and 6 μL was loaded on to a 20% gel run at 160 V for ~2 hours. The gel was stained with SYBR II fluorescent dye and imaged. The fluorescent bands were quantitated and analyzed as the integrated optical density (IOD).

Figure 18:
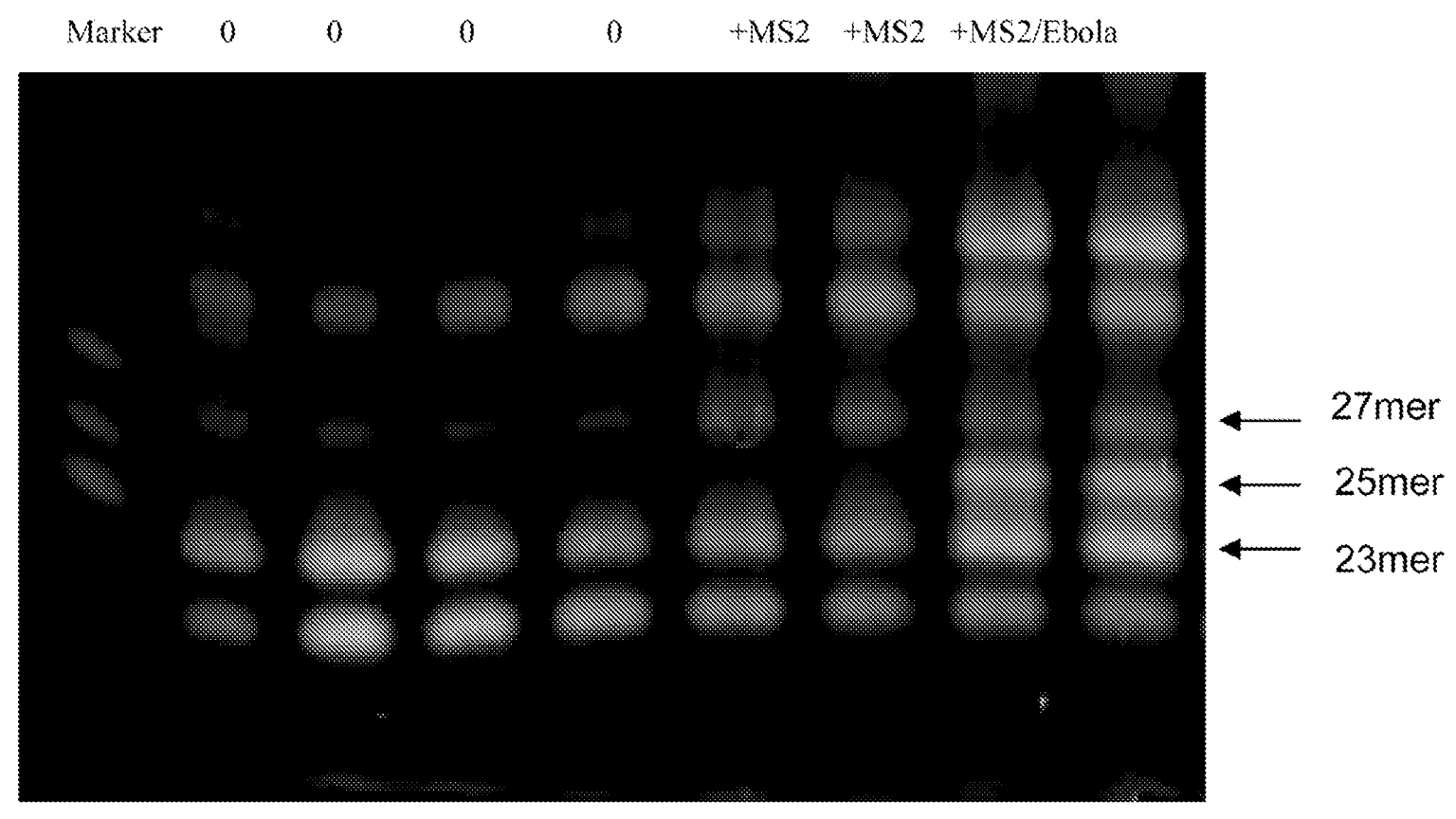

FIG. 18. Gel electrophoresis results for the MS2/Ebola RNA duplex reaction.

The NEAR reaction including templates for both a MS2 and Ebola assay was run in the absence of target RNA (negative, lanes 2-5), in the presence of MS2 only (27 mer product, lanes 6 and 7), and in the presence of both MS2 and Ebola RNA (27 mer and 25 mer product respectively, lanes 8 and 9). The target copy number used in this assay was 1E+6 copies. The assay was run for 10 min at 57° C. Templates varied in concentration between the assays to control the amplification. Samples were run on a 20% polyacrylamide gel at 160 V for ~2.5 hours. The gel was stained with SYBR II fluorescent dye and imaged. The fluorescent bands were quantitated and analyzed as the integrated optical density (IOD).

Figure 19:
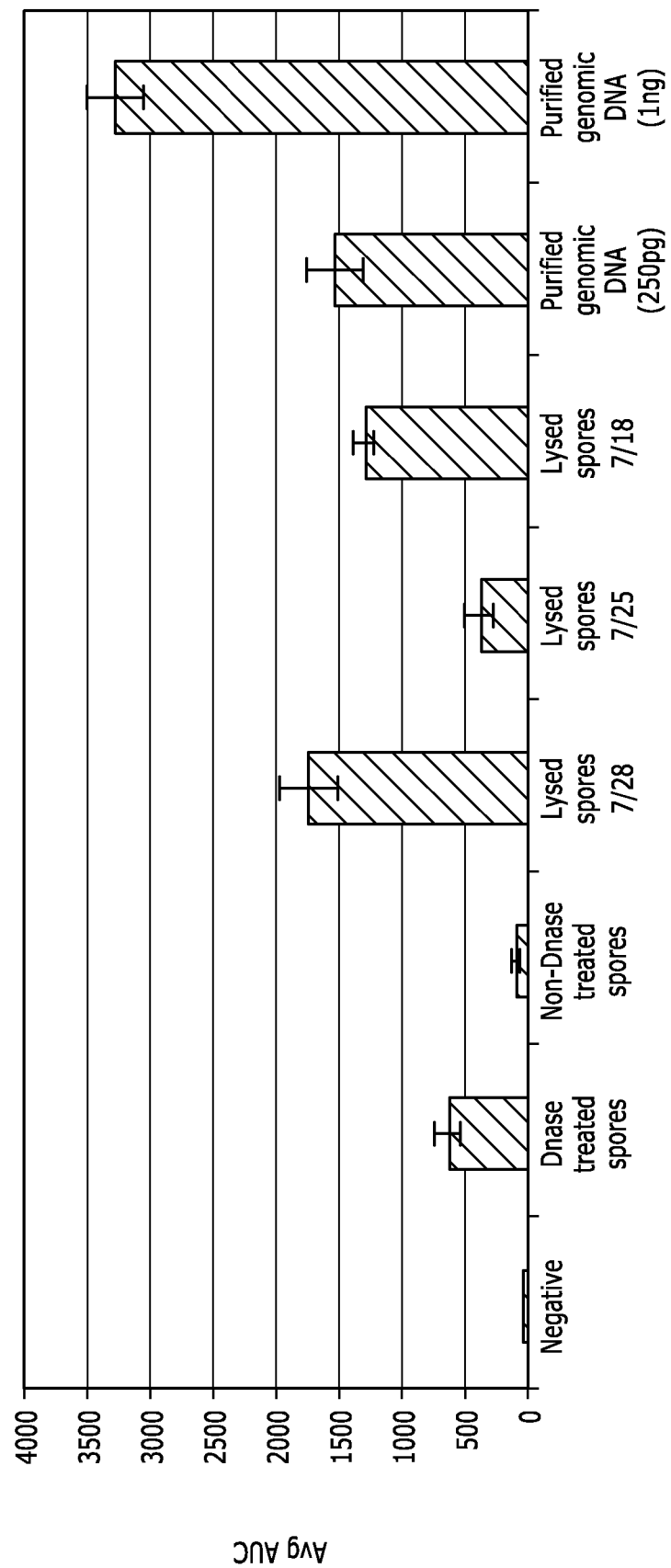

FIG. 19. Mass spec analysis of NEAR amplification of DNA from lysed spores.

Average AUC values from amplified product masses compared for lysed and unlysed samples. Lysed spore samples were then added to NEAR master mix and run for 10 minutes at 55° C., heat denatured for 4 minutes at 94° C., and run on the mass spec for analysis. AUC values of product peaks were averaged and compared (n=3).

Figure 20:
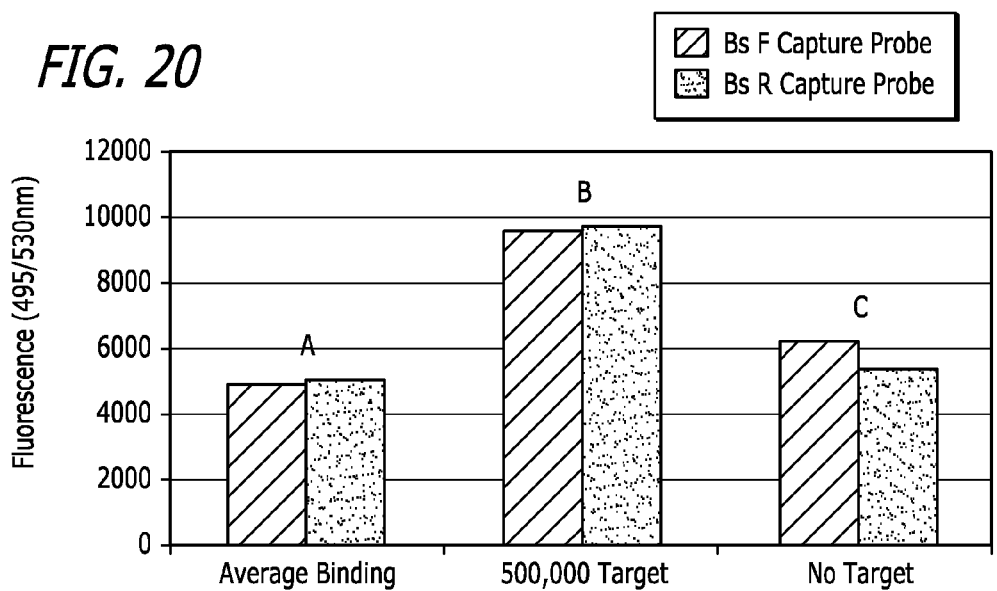

FIG. 20. Demonstration of the capture and extension approach for surface detection of the NEAR assay.

A.) Average binding (NEAR positive reaction product with no added polymerase), B.) 500,000 target (NEAR positive reaction product with added polymerase), and C.) No target (NEAR negative reaction with added polymerase) are compared. The NEAR assay was run for 10 minutes at 55° C., heat denatured at 94° C. for 4 minutes, then added to the plate with capture probe bound to the surface on the 5' end. Polymerase is added to one well of the positive reaction. The plate is incubated at 55° C. for 30 min, washed, SYBR II added, washed 3 times, and read on a Tecan plate reader (495 nm excitation/530 nm emission).

Figure 21:
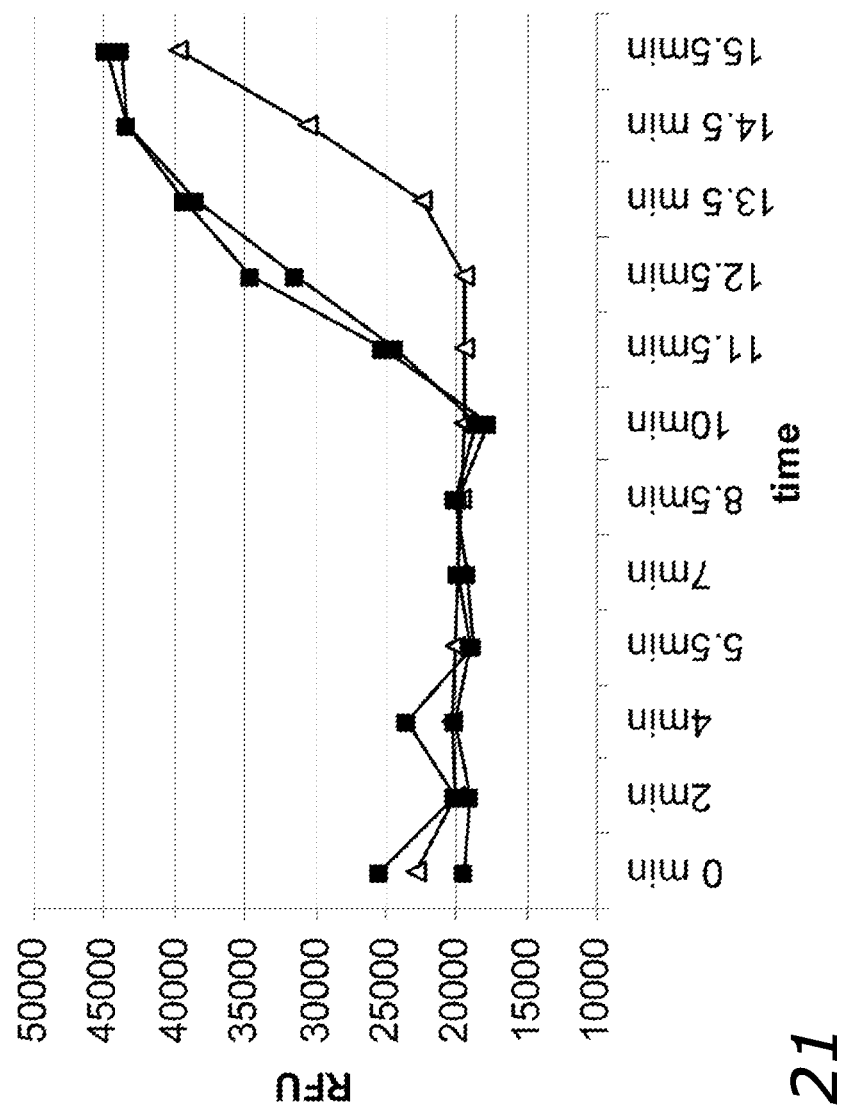

FIG. 21. Pseudo-real-time fluorescence detection of the NEAR FRET assay with a single template immobilized on a surface in the presence (squares) and absence (open triangles) of 1E+6 copies of genomic DNA.

NEAR reaction was performed in flat bottom 96-well plates covered with neutravidin. Solution of 1 µM FRET-labeled reverse template was incubated with gentle mixing for 1 hr at 37° C. Wells were washed 3 times with a PBS-Tween solution to release unbound template. NEAR reaction mix was added to the wells (one for each time point taken) and incubated at 58° C. on a heating block in a shaking incubator set to 135 RPM. Time points were taken by adding 1 µL EDTA to the well to stop the reaction. The fluorescence was read from the bottom using a Tecan 100 plate reader.

DETAILED DESCRIPTION

Provided herein are methods for the exponential amplification of short DNA or RNA sequences.

Target nucleic acids of the present invention include double-stranded and single-stranded nucleic acid molecules. The nucleic acid may be, for example, DNA or RNA. Where the target nucleic acid is an RNA molecule, the molecule may be, for example, double-stranded, single-stranded, or the RNA molecule may comprise a target sequence that is single-stranded. Target nucleic acids include, for example, genomic, plasmid, mitochondrial, cellular, and viral nucleic acid. The target nucleic acid may be, for example, genomic, chromosomal, plasmid DNA, a gene, any type of cellular RNA, or a synthetic oligonucleotide. By "genomic nucleic acid" is meant any nucleic acid from any genome, for example, including animal, plant, insect, and bacterial genomes, including, for example, genomes present in spores. Target nucleic acids further include microRNAs and siRNAs.

MicroRNAs, miRNAs, or small temporal RNAs (stRNAs), are short single-stranded RNA sequences, about 21-23 nucleotides long that are involved in gene regulation. MicroRNAs are thought to interfere with the translation of messenger RNAs as they are partially complementary to messenger RNAs. (see, for example, Ruvkun, Gl, Science 294:797-99 (2001); Lagos-Quintana, M., et al., Science 294:854-58 (2001); Lau, N. C., et al, Science 294:858-62 (2001); Lee, R. C., and Ambros, V., Science 294:862-64 (2001); Baulcombe, D., et al., Science 297:2002-03 (2002); Llave, C., Science 297:2053-56 (2002); Hutvagner, G., and Zamore, P. D., Science 297:2056-60 (2002)). MicroRNA may also have a role in the immune system, based on studies recently reported in knock-out mice. (see, for example, Wade, N., "Studies Reveal and Immune System Regulator" New York Times, Apr. 27, 2007). MicroRNA precursors that may also be detected using the methods of the present invention include, for example, the primary transcript (pri-miRNA) and the pre-miRNA stem-loop-structured RNA that is further processed into miRNA.

Short interfering RNAs, or siRNAs are at least partially double-stranded, about 20-25 nucleotide long RNA molecules that are found to be involved in RNA interference, for example, in the down-regulation of viral replication or gene expression (see for example Zamore et al., 2000, Cell, 101, 25-33; Bass, 2001, Nature, 411, 428-429; Elbashir et al., 2001, Nature, 411, 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237; Hutvagner and Zamore, 2002, Science, 297, 2056-60; McManus et al., 2002, RNA, 8, 842-850; Reinhart et al., 2002, Gene & Dev., 16, 1616-1626; and Reinhart & Bartel, 2002, Science, 297, 1831).

The use of the term "target sequence" may refer to either the sense or antisense strand of the sequence, and also refers to the sequences as they exist on target nucleic acids, amplified copies, or amplification products, of the original target sequence. The amplification product may be a larger molecule that comprises the target sequence, as well as at least one other sequence, or other nucleotides. The length of the target sequence, and the guanosine:cytosine (GC) concentration (percent), is dependent on the temperature at which the reaction is run; this temperature is dependent on the stability of the polymerases and nicking enzymes used in the reaction. Those of ordinary skill in the art may run sample assays to determine the appropriate length and GC concentration for the reaction conditions. For example, where the polymerase and nicking enzyme are stable up to 60° C., then the target sequence may be, for example, from 19 to 50 nucleotides in length, or for example, from 20 to 45, 20 to 40, 22-35, or 23 to 32 nucleotides in length. The GC concentration under these conditions may be, for example, less than 60%, less than 55%, less than 50%, or less than 45%. The target sequence should not contain nicking sites for any nicking enzymes that will be included in the reaction mix.

The target sequences may be amplified in many types of samples including, but not limited to samples containing spores, viruses, cells, nucleic acid from prokaryotes or eukaryotes, or any free nucleic acid. For example, the assay can detect the DNA on the outside of spores without the need for lysis. The sample may be isolated from any material suspected of containing the target sequence. For example, for animals, for example, mammals, such as, for example, humans, the sample may comprise blood, bone marrow, mucus, lymph, hard tissues, for example, liver, spleen, kidney, lung, or ovary, biopsies, sputum, saliva, tears, feces, or urine. Or, the target sequence may be present in air, plant, soil, or other materials suspected of containing biological organisms.

Target sequences may be present in samples that may also contain environmental and contaminants such as dust, pollen, and diesel exhaust, or clinically relevant matrices such as urine, mucus, or saliva. Target sequences may also be present in waste water, drinking water, air, milk, or other food. Depending on the concentration of these contaminants, sample purification methods known to those of ordinary skill in the art may be required to remove inhibitors for successful amplification. Purification may, for example, involve the use of detergent lysates, sonication, vortexing with glass beads, or a French press. This purification could also result in concentration of the sample target. Samples may also, for be further purified, for example, by filtration, phenol extraction, chromatography, ion exchange, gel electrophoresis, or density dependent centrifugation. The sample can be added directly to the reaction mix or pre-diluted and then added.

An oligonucleotide is a molecule comprising two or more deoxyribonucleotides or ribonucleotides, for example, more than three. The length of an oligonucleotide will depend on how it is to be used. The oligonucleotide may be derived synthetically or by cloning.

The term "complementary" as it refers to two nucleic acid sequences generally refers to the ability of the two sequences to form sufficient hydrogen bonding between the two nucleic acids to stabilize a double-stranded nucleotide sequence formed by hybridization of the two nucleic acids.

As used herein, "hybridization" and "binding" are used interchangeably and refer to the non-covalent binding or "base pairing" of complementary nucleic acid sequences to one another. Whether or not a particular probe remains base paired with a polynucleotide sequence depends on the degree of complementarity, the length of the probe, and the stringency of the binding conditions. The higher the stringency, the higher must be the degree of complementarity, and/or the longer the probe for binding or base pairing to remain stable.

As used herein, "stringency" refers to the combination of conditions to which nucleic acids are subjected that cause double-stranded nucleic acid to dissociate into component single strands such as pH extremes, high temperature, and salt concentration. The phrase "high stringency" refers to hybridization conditions that are sufficiently stringent or restrictive such that only specific base pairings will occur. The specificity should be sufficient to allow for the detection of unique sequences using an oligonucleotide probe or closely related sequence under standard Southern hybridization protocols (as described in J. Mol. Biol. 98:503 (1975)).

Templates are defined as oligonucleotides that bind to a recognition region of the target and also contain a nicking enzyme binding region upstream of the recognition region and a stabilizing region upstream to the nicking enzyme binding region.

By "recognition region" is meant a nucleic acid sequence on the template that is complementary to a nucleic acid sequence on the target sequence. By "recognition region on the target sequence" is meant the nucleotide sequence on the target sequence that is complementary to, and binds to, the template.

By "stabilizing region" is meant a nucleic acid sequence having, for example, about 50% GC content, designed to stabilize the molecule for, for example, the nicking and/or extension reactions.

In describing the positioning of certain sequences on nucleic acid molecules, such as, for example, in the target sequence, or the template, it is understood by those of ordinary skill in the art that the terms "3'" and "5'" refer to a location of a particular sequence or region in relation to another. Thus, when a sequence or a region is 3' to or 3' of another sequence or region, the location is between that sequence or region and the 3' hydroxyl of that strand of nucleic acid. When a location in a nucleic acid is 5' to or 5' of another sequence or region, that means that the location is between that sequence or region and the 5' phosphate of that strand of nucleic acid.

The polymerase is a protein able to catalyze the specific incorporation of nucleotides to extend a 3' hydroxyl terminus of a primer molecule, such as, for example, the template oligonucleotide, against a nucleic acid target sequence. The polymerase may be, for example, thermophilic so that it is active at an elevated reaction temperature. It may also, for example, have strand displacement capabilities. It does not, however, need to be very processive (30-40 nucleotides for a single synthesis is sufficient). If the polymerase also has reverse transcription capabilities (such as Bst (large fragment), 9° N, THERMINATOR, THERMINATOR II, etc.) the reaction can also amplify RNA targets in a single step without the use of a separate reverse transcriptase. More than one polymerase may be included in the reaction, in one example one of the polymerases may have reverse transcriptase activity and the other polymerase may lack reverse transcriptase activity. The polymerase may be selected from, for example, the group consisting of one or more of the polymerases listed in Table 1.

TABLE 1

| Polymerase |
| --- |
| Bst DNA polymerase |
| Bst DNA polymerase (Large fragment) |
| 9°Nm DNA polymerase |
| Phi29 DNA polymerase |
| DNA polymerase I (*E. coli*) |
| DNA polymerase I, Large (Klenow) fragment |
| Klenow fragment (3'-5' exo-) |
| T4 DNA polymerase |
| T7 DNA polymerase |
| Deep Vent$_R$ ™ (exo-) DNA Polymerase |
| Deep Vent$_R$ ™ DNA Polymerase |
| DyNAzyme ™ EXT DNA |
| DyNAzyme ™ II Hot Start DNA Polymerase |
| Phusion ™ High-Fidelity DNA Polymerase |
| Therminator ™ DNA Polymerase |
| Therminator ™ II DNA Polymerase |
| Vent$_R$ ® DNA Polymerase |
| Vent$_R$ ® (exo-) DNA Polymerase |
| RepliPHI ™ Phi29 DNA Polymerase |
| rBst DNA Polymerase |
| rBst DNA Polymerase, Large Fragment (IsoTherm ™ DNA Polymerase) |
| MasterAmp ™ AmpliTherm ™ DNA Polymerase |
| Taq DNA polymerase |
| Tth DNA polymerase |
| Tfl DNA polymerase |
| Tgo DNA polymerase |
| SP6 DNA polymerase |
| Tbr DNA polymerase |
| DNA polymerase Beta |
| ThermoPhi DNA polymerase |

"Nicking" refers to the cleavage of only one strand of the double-stranded portion of a fully or partially double-stranded nucleic acid. The position where the nucleic acid is nicked is referred to as the nicking site or nicking enzyme site. The recognition sequence that the nicking enzyme recognizes is referred to as the nicking enzyme binding site. "Capable of nicking" refers to an enzymatic capability of a nicking enzyme.

The nicking enzyme is a protein that binds to double-stranded DNA and cleaves one strand of a double-stranded duplex. The nicking enzyme may cleave either upstream or downstream of the binding site, or nicking enzyme recognition site. In exemplary embodiments, the reaction comprises the use of nicking enzymes that cleave or nick downstream of the binding site (top strand nicking enzymes) so that the product sequence does not contain the nicking site. Using an enzyme that cleaves downstream of the binding site allows the polymerase to more easily extend without having to displace the nicking enzyme. The nicking enzyme must be functional in the same reaction conditions as the polymerase, so optimization between the two ideal conditions for both is necessary. Nicking enzymes are available from, for example, New England Biolabs (NEB) and Fermentas. The nicking enzyme may, for example, be selected from the group consisting of one or more of the nicking enzymes listed in Table 2.

TABLE 2

| Nicking Enzyme | Alternate Name |
| --- | --- |
| Nb.BbvCI | |
| Nb.Bpu10I | |
| Nb.BsaI | |
| Nb.BsmI | |
| Nb.BsrDI | |
| Nb.BstNBIP | |
| Nb.BstSEIP | |
| Nb.BtsI | |
| Nb.SapI | |
| Nt.AlwI | |
| Nt.BbvCI | |
| Nt.BhaIIIP | |
| Nt.Bpu10I | |
| Nt.Bpu10IB | |
| Nt.BsaI | |
| Nt.BsmAI | |
| Nt.BsmBI | |
| Nt.BspD6I | |
| Nt.BspQI | |
| Nt.Bst9I | |
| Nt.BstNBI | N.BstNB I |
| Nt.BstSEI | |
| Nt.CviARORFMP | |
| Nt.CviFRORFAP | |
| Nt.CviPII | Nt.CviPIIm |
| Nt.CviQII | |
| Nt.CviQXI | |
| Nt.EsaSS1198P | |
| Nt.MlyI | |
| Nt.SapI | |

Nicking enzymes may be, for example, selected from the group consisting of Nt.BspQI(NEB), Nb.BbvCI(NEB), Nb.BsmI(NEB), Nb.BsrDI(NEB), Nb.BtsI(NEB), Nt.AlwI (NEB), Nt.BbvCI(NEB), Nt.BstNBI(NEB), Nt.CviPII (NEB), Nb.Bpu10I(Fermantas), and Nt.Bpu10I(Fermentas). In certain embodiments, the nicking enzyme is selected from the group consisting of Nt.NBst.NBI, Nb.BsmI, and Nb.BsrDI. Those of ordinary skill in the art are aware that various nicking enzymes other than those mentioned specifically herein may be used in the methods of the present invention.

Nicking enzymes and polymerases of the present invention may be, for example, stable at room temperature, the enzymes may also, for example, be stable at temperatures up to 37° C., 42° C., 60° C., 65° C., 70° C., 75° C., 80° C., or 85° C. In certain embodiments, the enzymes are stable up to 60° C.

Product or amplified product is defined as the end result of the extension of the template along the target that is nicked, released, and then feeds back into the amplification cycle as a target for the opposite template.

A "native nucleotide" refers to adenylic acid, guanylic acid, cytidylic acid, thymidylic acid, or uridylic acid. A "derivatized nucleotide" is a nucleotide other than a native nucleotide.

The reaction may be conducted in the presence of native nucleotides, such as, for example, dideoxyribonucleoside triphosphates (dNTPs). The reaction may also be carried out in the presence of labeled dNTPs, such as, for example, radiolabels such as, for example, $^{32}P$, $^{33}P$, $^{125}I$, or $^{35}S$, enzyme labels such as alkaline phosphatase, fluorescent labels such as fluorescein isothiocyanate (FITC), biotin, avidin, digoxigenin, antigens, haptens, or fluorochromes. These derivatized nucleotides may, for example, be present in the templates.

By "constant temperature," "isothermal conditions" or "isothermally" is meant a set of reaction conditions where the temperature of the reaction is kept essentially constant during the course of the amplification reaction. An advantage of the amplification method of the present invention is that the temperature does not need to be cycled between an upper temperature and a lower temperature. The nicking and the extension reaction will work at the same temperature or within the same narrow temperature range. However, it is not necessary that the temperature be maintained at precisely one temperature. If the equipment used to maintain an elevated temperature allows the temperature of the reaction mixture to vary by a few degrees, this is not detrimental to the amplification reaction, and may still be considered to be an isothermal reaction.

The term "multiplex amplification" refers to the amplification of more than one nucleic acid of interest. For example, it can refer to the amplification of multiple sequences from the same sample or the amplification of one of several sequences in a sample as discussed, for example, in U.S. Pat. Nos. 5,422,252; and 5,470,723, which provide examples of multiplex strand displacement amplification. The term also refers to the amplification of one or more sequences present in multiple samples either simultaneously or in step-wise fashion.

Template Design

Forward and Reverse templates are designed so that there is a stabilizing region at the 5' end, a nicking site downstream of the stabilizing region, and a recognition region downstream of the nicking site on the 3' end of the oligonucleotide. The total oligo length can range from 19 to 40, for example from 19-40, 23-40, 20-24, 23-24, 23-32, 25-40, 27-40, or 27-35 nucleotides depending on the length of each individual region, the temperature, the length of the target sequence, and the GC concentration. The templates may be designed so that they, together, would bind to less than or equal to 100% of the target sequence, one binding to the sense strand, and one to the antisense strand. For example, where the forward template binds to about 60% of the target antisense strand, the reverse template may, for example, bind to about 40% of the target sense strand. The templates may be designed to allow for spacer bases on the target sequence, that do not bind to either template. The templates thus may be designed to bind to about 30%, about 40%, about 50%, or about 60% of the target sequence.

The recognition region of the forward template is designed to be identical to the 5' region of the target sense strand and complementary to the 3' end of the target site antisense strand, for example, 8-16, 9-16, 10-16, 10-15, or 11-14 nucleotides long. In exemplary embodiments, the length is 12-13 nucleotides. The recognition region of the reverse template is designed to be complementary to the 3' end of the target site sense strand, for example, 8-16, 9-16, 10-16, 10-15, or 11-14 nucleotides long. In exemplary embodiments, the length is 12-13 nucleotides.

In certain embodiments, the lengths of the recognition regions are adjusted so that there is at least one nucleotide in the target sequence that is not in the forward template's recognition region and also does not have its complement in the reverse template's recognition region. These spacer bases are nucleotides contained within the target sequence that lie in between the 3' ends of the forward and reverse templates. In certain embodiments, 5 spacer bases or less are present in the target sequence. In exemplary embodiments, the number of spacer bases is 2 to 3. In certain embodiments, the number of spacer bases is 1, 2, 3, 4, or 5. These spacer bases allow for distinction of the true amplified product from any background products amplified by extension due to overlapping templates in a similar manner to primer-dimers. This consideration allows for improved discrimination between background and amplification of true target. However, these spacer bases are not required for the amplification to proceed.

The nicking site sequence of the template depends on which nicking enzyme is chosen for each template. Different nicking enzymes may be used in a single assay, but a simple amplification may, for example, employ a single nicking enzyme for use with both templates. Thus, the embodiments of the present invention include those where both templates comprise recognition sites for the same nicking enzyme, and only one nicking enzyme is used in the reaction. In these embodiments, both the first and second nicking enzymes are the same. The present invention also includes those embodiments where each template comprises a recognition site for a different nicking enzyme, and two nicking enzymes are used in the reaction.

For example, in the case of Nt.BstNBI, the enzyme binding site is 5'-GAGTC-3' and the enzyme nicks the top strand four nucleotides down stream of this site (i.e., GAGTCNNNN^). The amplification reaction shows little dependence on the sequence of these four nucleotides (N), though optimal sequence of this region is 25% or less GC content and with a thymine adjacent to the 5' nucleotide of the binding region. The latter stipulation allows for the priming ability of products that have an additional adenine added on by the polymerase. The sequence of the four nucleotides can be optimized to create or eliminate the presence of hairpins, self-dimers, or heterodimers, depending on the application.

The stabilizing region on the 5' end of the template oligonucleotide is designed to be roughly 50% GC. Thus, the GC content may be, for example, about 40%-60%, about 42%-58%, about 44%-56%, about 46%-54%, about 48%-52%, or about 49%-51%. These parameters result in a stabilizing region length of 8-11 nucleotides for the Nt.BstNBI enzyme, though lengths as short as 6 and as long as 15 nucleotides have been tested and were shown to work in this amplification method. Longer stabilizing regions or increased % GC to greater than 50% could further stabilize the nicking and extension reactions at higher reaction temperatures. The sequence of the 5' stabilizing regions of forward and reverse templates are usually identical, but can be varied if the aim is to capture each product strand independently. The sequence of this region should not interfere with the nicking site or the recognition region, though short internal hairpins within the template sequence have been shown to have improved real-time results.

The templates of the present invention may include, for example, spacers, blocking groups, and modified nucleotides. Modified nucleotides are nucleotides or nucleotide triphosphates that differ in composition and/or structure from natural nucleotide and nucleotide triphosphates. Modified nucleotide or nucleotide triphosphates used herein may, for example, be modified in such a way that, when the modifications are present on one strand of a double-stranded nucleic acid where there is a restriction endonuclease recognition site, the modified nucleotide or nucleotide triphosphates protect the modified strand against cleavage by restriction enzymes. Thus, the presence of the modified nucleotides or nucleotide triphosphates encourages the nicking rather than the cleavage of the double-stranded nucleic acid. Blocking groups are chemical moieties that can be added to the template to inhibit target sequence-independent nucleic acid polymerization by the polymerase. Blocking groups are usually located at the 3' end of the template. Examples of blocking groups include, for example, alkyl groups, non-nucleotide linkers, phosphorothioate, alkanediol residues, peptide nucleic acid, and nucleotide derivatives lacking a 3'-OH, including, for example, cordycepin. Examples of spacers, include, for example, C3 spacers. Spacers may be used, for example, within the template, and also, for example, at the 5' end, to attach other groups, such as, for example, labels.

Detailed Mechanism of Amplification

NEAR amplification requires the presence of a nucleic acid target, at least two template oligonucleotides, a thermophilic nicking enzyme, a thermophilic polymerase, and buffer components all held at the reaction temperature. The recognition region of the templates interacts with the complementary target sequence. Since the melting temperature of the complementary regions of the target and template is well below the reaction temperature, the interaction between the two nucleic acid strands is transient, but allows enough time for a thermophilic polymerase to extend from the 3' end of the template along the target strand. Experiments have shown that certain polymerases bind to single-stranded oligonucleotides. The pre-formation of this complex can facilitate the speed of the amplification process.

Figure 1A:
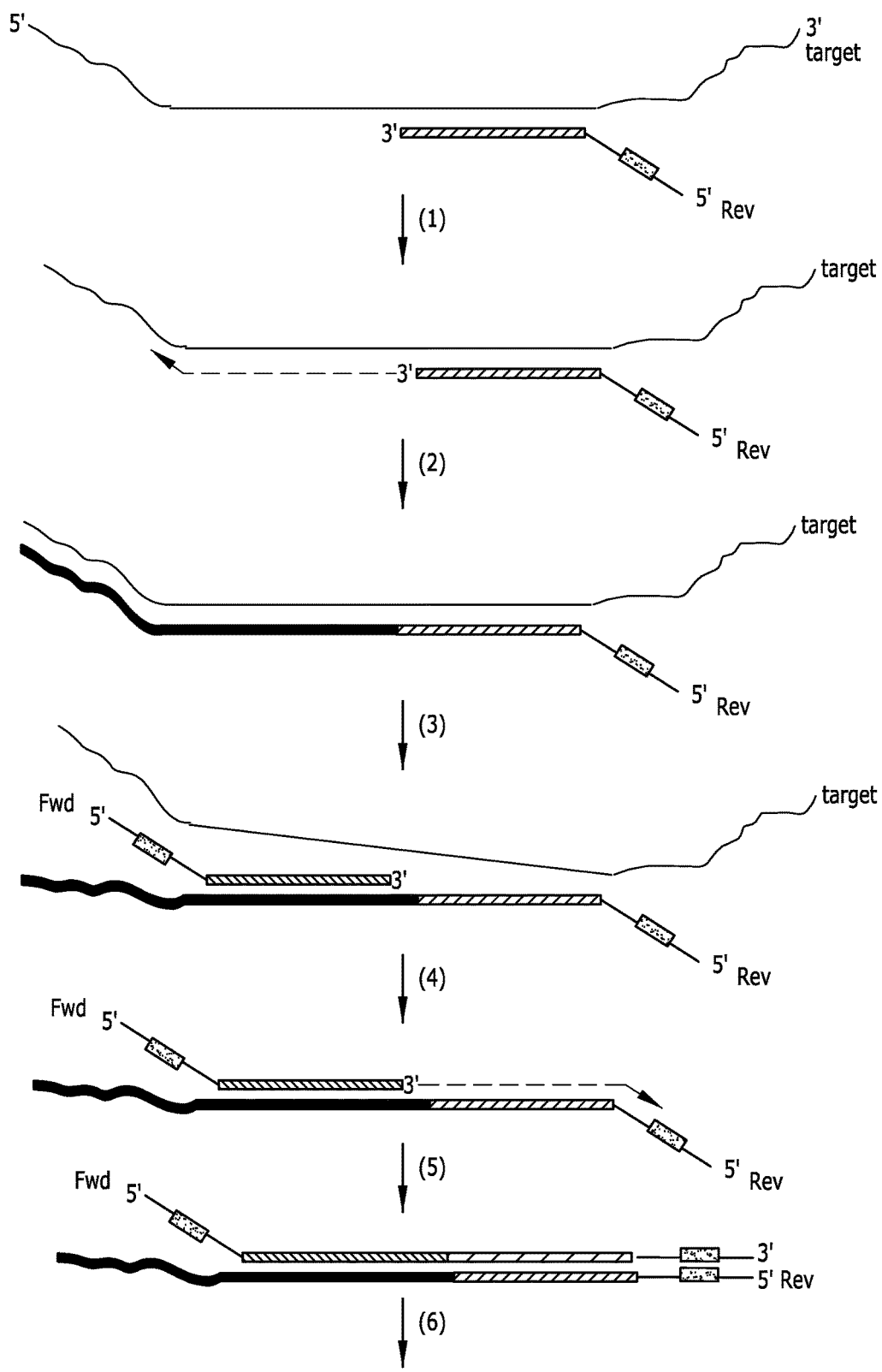
FIGS. 1A-D are graphic drawings depicting mechanisms of the reactions of the present invention.
Figure 1B:
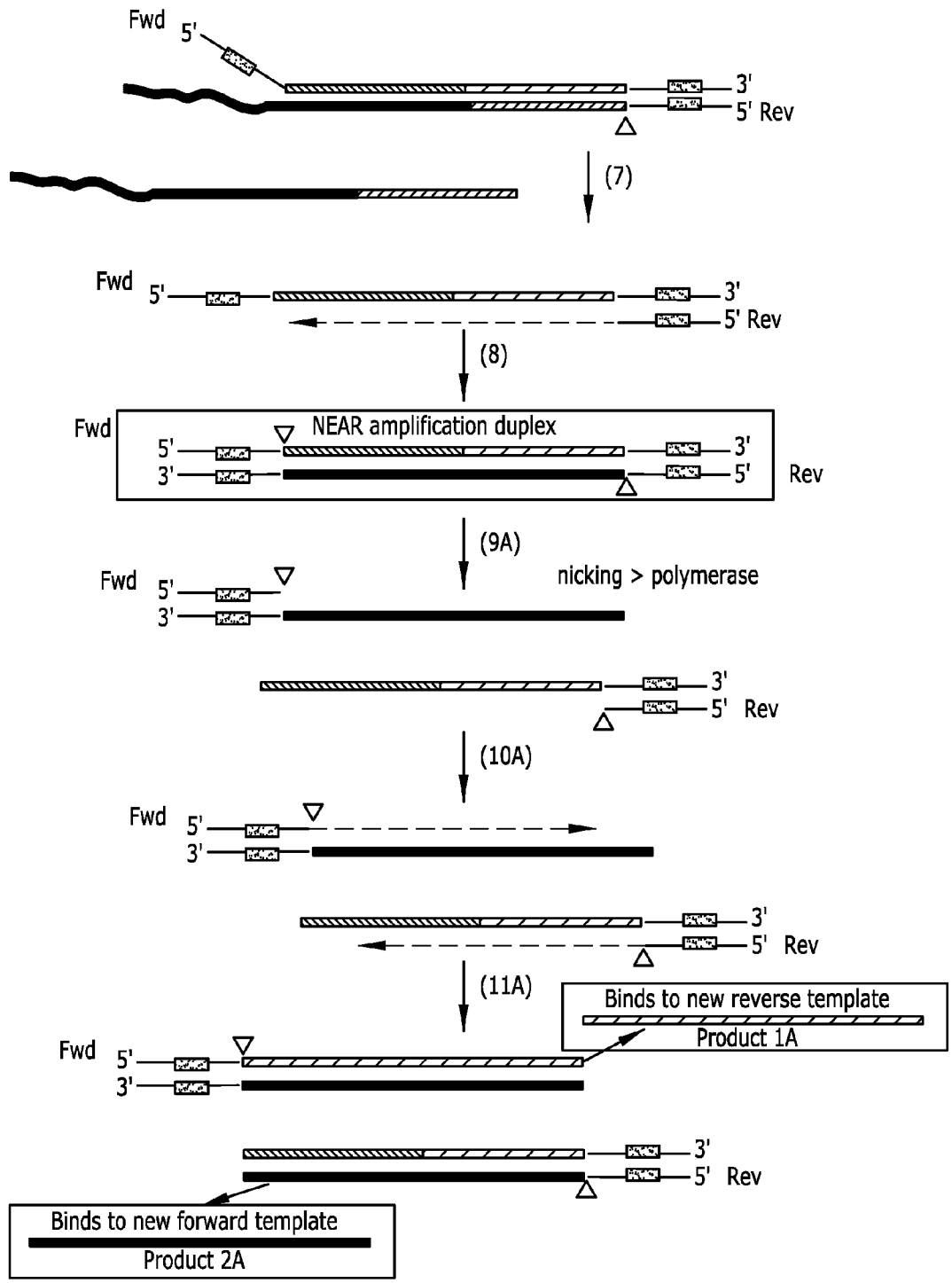
Figures 1C, 1D:
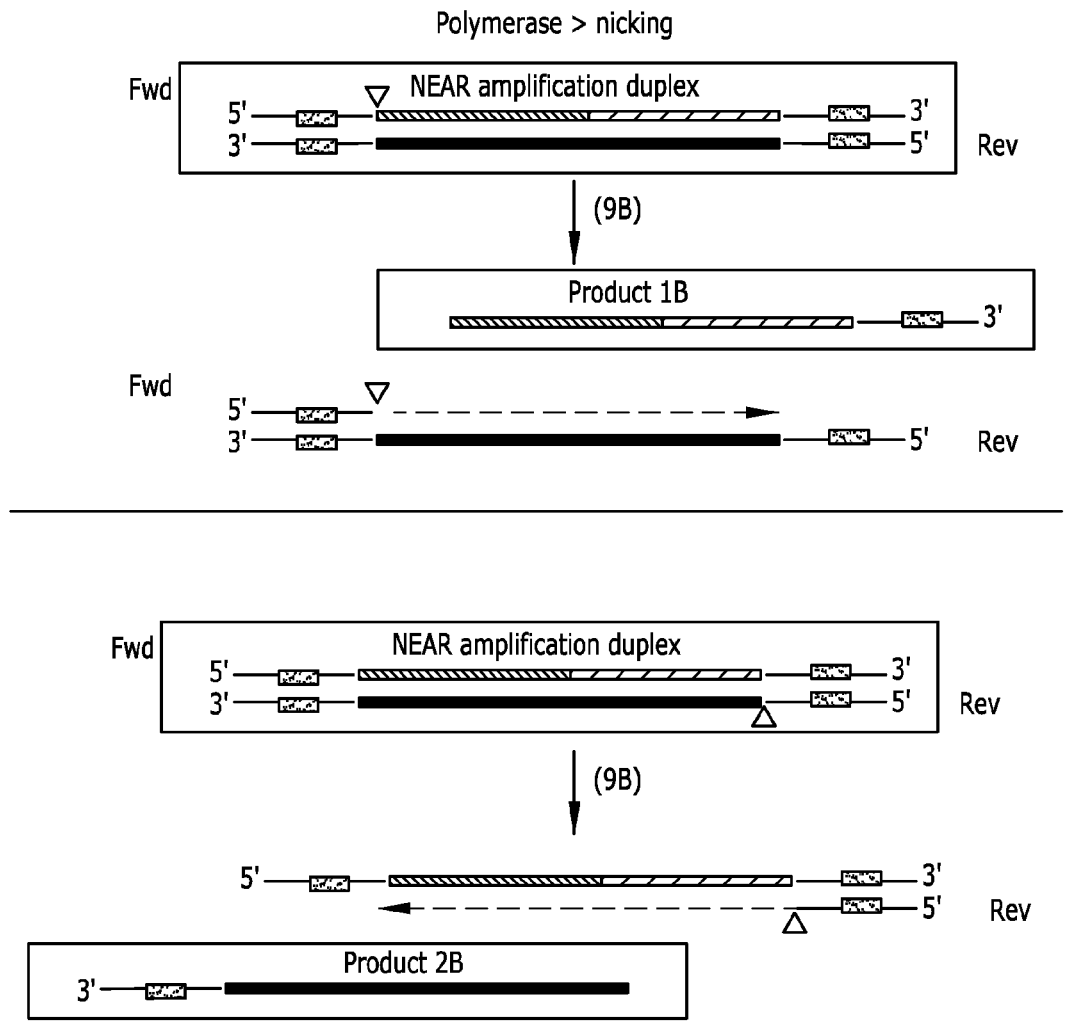

For a double-stranded target, both templates can interact with the corresponding target strands simultaneously (forward template with the antisense strand and reverse template with the sense strand) during the normal breathing of double-stranded DNA. The target may also be generated by a single or double nick sites within the genome sequence. For a single-stranded target (either RNA or DNA), the reverse template binds and extends first (FIG. 1, Step 1 and 2). The extended sequence contains the complement to the forward template. The forward template then displaces a region of the target and binds to the 3' synthesized region complementary to the recognition region of the forward template (Step 3). Alternatively, another reverse template can also displace the initial extended reverse template at the recognition region to create a single-stranded extended reverse template for the forward template to bind. The initial binding and extension of the templates is facilitated by a non-processive polymerase that extends shorter strands of DNA so that the melting temperature of the synthesized product is at or near the reaction temperature; therefore, a percentage of the product becomes single-stranded once the polymerase dissociates. The single-stranded product is then available for the next template recognition site to bind and polymerase to extend.

The forward template is extended to the 5' end of the reverse template, creating a double-stranded nicking enzyme binding site for the reverse template (Step 5). The nicking enzyme then binds to the duplex and nicks directly upstream of the recognition sequence of the reverse template strand (in the case of a top-strand nicking enzyme) (Step 6). The nucleic acid sequence downstream of the nick is either released (if the melting temperature is near the reaction temperature) and/or is displaced by the polymerase synthesis from the 3'-OH nick site. Polymerase extends along the forward template to the 5' end of the forward template (Step 8). The double-strand formed from the extension of both templates creates a nicking enzyme binding site on either end of the duplex. This double-strand is termed the NEAR amplification duplex. When nicking enzyme binds and nicks, either the target product located in between the two nick sites (with 5'-phosphate and 3'-OH) is released, usually ranging in length from (but is not limited to) 23 to 29 bases (Steps 9-11A), or the singly-nicked product containing the target product and the reverse complement of the nick site and stability region of the template (usually 36 to 48 bases in length) is released (Steps 9-11B). The ratio of products 1 to 2 can be adjusted by varying the concentrations of the templates. The forward:reverse template ratio may vary from, for example, molar ratios of 100:1, 75:1; 50:1, 40:1, 30:1, 20:1, 10:1, 5:1, 2.5:1, 1:1, 1:2.5, 1:5, 1:10, 1:20, 1:30, 1:40, 1:50, 1:75, or 1:100. The ratio of products (A to B) is dependent on the ratio of nicking enzyme to polymerase, i.e. a higher concentration of polymerase results in more of the longer length product (B) since there is comparatively less nicking enzyme to nick both strands simultaneously before the polymerase extends. Since displaced/released product of the reverse template feeds into the forward template and vice versa, exponential amplification is achieved. The nicking enzyme:polymerase ratio may vary from, for example, enzyme unit ratios of 20:1, 15:1; 10:1, 5:1, 4:1, 3:1, 2:1, 1.5:1, 1:1, 1:1.5, 1:2, 1:3, 1:4, 1:5, 1:10, 1:15, 1:20. In certain embodiments, the ratio of nicking enzyme to polymerase may, for example, be 1:3, 1:2, 1:1.5, or 1:0.8. Those of ordinary skill in the art recognize that these ratios may represent rounded values. This nicking and polymerase extension process continues until one of the resources (usually dNTPs or enzyme) is exhausted.

The time that the reaction is run may vary from, for example, 1-20 minutes, or 1-10, 1-8, 1-5, 1-2.5, 2.5-5, 2.5-8, 2.5-10, or 2.5-20 minutes.

The methods of the present invention do not require the use of temperature cycling, as often is required in methods of amplification to dissociate the target sequence from the amplified nucleic acid. The temperature of the reaction may vary based on the length of the sequence, and the GC concentration, but, as understood by those of ordinary skill in the art, the temperature should be high enough to minimize non-specific binding. The temperature should also be suitable for the enzymes of the reaction, the nicking enzyme and the polymerase. For example, the reaction may be run at 37° C.-85° C., 37° C.-60° C., 54° C.-60° C., and, in exemplary embodiments, from 55° C.-59° C.

The polymerase may be mixed with the target nucleic acid molecule before, after, or at the same time as, the nicking enzyme. In exemplary embodiments, a reaction buffer is optimized to be suitable for both the nicking enzyme and the polymerase.

Reactions may be allowed to completion, that is, when one of the resources is exhausted. Or, the reaction may be stopped using methods known to those of ordinary skill in the art, such as, for example, heat denaturation, or the addition of EDTA, high salts, or detergents. In exemplary embodiments, where mass spectrometry is to be used following amplification, EDTA may be used to stop the reaction.

Reaction Components

In a 1.5 mL Eppendorf tube combine the following reagents in order from top to bottom:

| Reagent Added: | μL Per Reaction |
|---|---|
| H$_2$O | 31.4 |
| 10X Thermopol Buffer (NEB) | 5 |
| 10X NEB Buffer 3 | 2.5 |
| 100 mM MgSO$_4$ | 4.5 |
| 10 mM dNTPs | 1.5 |
| 8 U/μl Bst Pol | 0.6 |
| 10 U/μl N.BstNBI | 1.5 |
| 20 μM Forward Template | 0.25 |
| 20 μM Reverse Template | 0.25 |
| Total reaction mixture | 47.5 |
| Target sample | 2.5 |
| Total Reaction Volume | 50 μL |

The concentrations of components for the reaction conditions in this example are as follows:

| Concentration | Component |
|---|---|
| 45.7 mM | Tris-HCl |
| 13.9 mM | KCl |
| 10 mM | (NH$_4$)$_2$SO$_4$ |
| 50 mM | NaCl |
| 0.5 mM | DTT |
| 15 mM | MgCl$_2$ |
| 0.10% | Triton X-100 |
| 0.008 mM | EDTA |
| 6 μg/mL | BSA |
| 3.90% | Glycerol (can be lower if using a more concentrated enzyme stock) |
| 0.3 U/uL | Nt.BstNBI |
| 0.1-0.4 U/μL | Bst polymerase (large fragment) |
| 0.1 μM | Forward template |
| 0.1 μM | Reverse template |

Variations in buffer conditions, MgSO$_4$ concentration, polymerase concentration, and template concentrations all can be optimized based on the assay sequence and desired detection method. The amount of glycerol may, for example, be lowered if a more concentrated enzyme stock is used. Also, those of ordinary skill in the art recognize that the reaction may be run without EDTA or BSA; these components may be present in the reaction as part of the storage buffers for the enzymes. The volumes can be scaled for larger or smaller total reaction volumes. The volume is usually between 5 μL and 100 μL.

The template concentrations are typically in excess of the concentration of target. The concentrations of the forward and reverse templates can be at the same or at different concentrations to bias the amplification of one product over the other. The concentration of each is usually between 10 nM and 1 μM.

Additives such as BSA, non-ionic detergents such as TRITON X-100 or TWEEN 20, DMSO, DTT, and RNase inhibitor may be included for optimization purposes without adversely affecting the amplification reaction.

Preparing/Adding Target

Targets may be diluted in 1× Thermopol Buffer II, 1×TE (pH 7.5) or $H_2O$. Hot start conditions allow for faster, more specific amplification. In this case, the reaction mix (minus either enzymes or templates and target) is heated to the reaction temperature for 2 minutes, after which the reaction mix is added to the other component (enzymes or templates/target). The target can be added in any volume up to the total amount of water required in the reaction. In this case, the target would be diluted in water. In the example above for a 50 µL total reaction volume, 2.5 µL of the prepared target should be added per reaction to bring the total reaction volume to 50 µL.

Running the Reaction

The reaction is run at a constant temperature, usually between 54° C. and 60° C. for the enzyme combination of Bst polymerase (large fragment) and Nt.Bst.NB1 nicking enzyme. Other enzyme combinations may be used and the optimal reaction temperature will be based on the optimal temperature for both the nicking enzyme and polymerase to work in concert as well as the melting temperature of the reaction products. The reaction is held at temperature for 2.5 to 10 minutes until the desired amount of amplification is achieved. The reaction may be stopped by either a heat denaturation step to denature the enzymes (when using enzymes that can be heat-killed). Alternatively, the reaction may be stopped by adding EDTA to the reaction.

Readout

The amplified target sequence may be detected by any method known to one of ordinary skill in the art. By way of non-limiting example, several of these known methods are presented herein. In one method, amplified products may be detected by gel electrophoresis, thus detecting reaction products having a specific length. The nucleotides may, for example, be labeled, such as, for example, with biotin. Biotin-labeled amplified sequences may be captured using avidin bound to a signal generating enzyme, for example, peroxidase.

Nucleic acid detection methods may employ the use of dyes that specifically stain double-stranded DNA. Intercalating dyes that exhibit enhanced fluorescence upon binding to DNA or RNA are a basic tool in molecular and cell biology. Dyes may be, for example, DNA or RNA intercalating fluorophores and may include but are not limited to the following examples: Acridine orange, ethidium bromide, Hoechst dyes, PICOGREEN, propidium iodide, SYBR I (an asymmetrical cyanine dye), SYBR II, TOTO (a thiaxole orange dimer) and YOYO (an oxazole yellow dimer). Dyes provide an opportunity for increasing the sensitivity of nucleic acid detection when used in conjunction with various detection methods and may have varying optimal usage parameters. For example ethidium bromide is commonly used to stain DNA in agarose gels after gel electrophoresis and during PCR (Hiquchi et al., Nature Biotechnology 10; 413-417, April 1992), propidium iodide and Hoechst 33258 are used in flow cytometry to determine DNA ploidy of cells, SYBR Green 1 has been used in the analysis of double-stranded DNA by capillary electrophoresis with laser induced fluorescence detection and PICOGREEN has been used to enhance the detection of double-stranded DNA after matched ion pair polynucleotide chromatography (Singer et al., Analytical Biochemistry 249, 229-238 1997).

Nucleic acid detection methods may also employ the use of labeled nucleotides incorporated directly into the target sequence or into probes containing complementary sequences to the target of interested. Such labels may be radioactive and/or fluorescent in nature and can be resolved in any of the manners discussed herein.

Methods of detecting and/or continuously monitoring the amplification of nucleic acid products are also well known to those skilled in the art and several examples are described below.

The production or presence of target nucleic acids and nucleic acid sequences may be detected and monitored by Molecular Beacons. Molecular Beacons are hair-pin shaped oligonucleotides containing a fluorophore on one end and a quenching dye on the opposite end. The loop of the hair-pin contains a probe sequence that is complementary to a target sequence and the stem is formed by annealing of complementary arm sequences located on either side of the probe sequence. A fluorophore and a quenching molecule are covalently linked at opposite ends of each arm. Under conditions that prevent the oligonucleotides from hybridizing to its complementary target or when the molecular beacon is free in solution the fluorescent and quenching molecules are proximal to one another preventing fluorescence resonance energy transfer (FRET). When the molecular beacon encounters a target molecule, hybridization occurs; the loop structure is converted to a stable more rigid conformation causing separation of the fluorophore and quencher molecules leading to fluorescence (Tyagi et al. Nature Biotechnology 14: March 1996, 303-308). Due to the specificity of the probe, the generation of fluorescence is exclusively due to the synthesis of the intended amplified product.

Molecular beacons are extraordinarily specific and can discern a single nucleotide polymorphism. Molecular beacons can also be synthesized with different colored fluorophores and different target sequences, enabling several products in the same reaction to be quantitated simultaneously. For quantitative amplification processes, molecular beacons can specifically bind to the amplified target following each cycle of amplification, and because non-hybridized molecular beacons are dark, it is not necessary to isolate the probe-target hybrids to quantitatively determine the amount of amplified product. The resulting signal is proportional to the amount of amplified product. This can be done in real time. As with other real time formats, the specific reaction conditions must be optimized for each primer/probe set to ensure accuracy and precision.

The production or presence of target nucleic acids and nucleic acid sequences may also be detected and monitored by Fluorescence resonance energy transfer (FRET). FRET is an energy transfer mechanism between two chromophores: a donor and an acceptor molecule. Briefly, a donor fluorophore molecule is excited at a specific excitation wavelength. The subsequent emission from the donor molecule as it returns to its ground state may transfer excitation energy to the acceptor molecule through a long range dipole-dipole interaction. The intensity of the emission of the acceptor molecule can be monitored and is a function of the distance between the donor and the acceptor, the overlap of the donor emission spectrum and the acceptor absorption spectrum and the orientation of the donor emission dipole moment and the acceptor absorption dipole moment. FRET is a useful tool to quantify molecular dynamics, for example, in DNA-DNA interactions as seen with Molecular Beacons. For monitoring the production of a specific product a probe can be labeled with a donor molecule on one end and an acceptor molecule on the other. Probe-target hybridization brings a change in the distance or orientation of the donor and acceptor and FRET change is observed. (Joseph R. Lakowicz, "Principles of Fluorescence Spectroscopy", Plenum Publishing Corporation, 2nd edition (Jul. 1, 1999)).

The production or presence of target nucleic acids and nucleic acid sequences may also be detected and monitored by Mass Spectrometry. Mass Spectrometry is an analytical technique that may be used to determine the structure and quantity of the target nucleic acid species and can be used to provide rapid analysis of complex mixtures. Following the method, samples are ionized, the resulting ions separated in electric and/or magnetic fields according to their mass-to-charge ratio, and a detector measures the mass-to-charge ratio of ions. (Crain, P. F. and McCloskey, J. A., Current Opinion in Biotechnology 9: 25-34 (1998)). Mass spectrometry methods include, for example, MALDI, MALDI/TOF, or Electrospray. These methods may be combined with gas chromatography (GC/MS) and liquid chromatography (LC/MS). MS has been applied to the sequence determination of DNA and RNA oligonucleotides (Limbach P., Mass Spectrom. Rev. 15: 297-336 (1996); Murray K., J. Mass Spectrom. 31: 1203-1215 (1996)). MS and more particularly, matrix-assisted laser desorption/ionization MS (MALDI MS) has the potential of very high throughput due to high-speed signal acquisition and automated analysis off solid surfaces. It has been pointed out that MS, in addition to saving time, measures an intrinsic property of the molecules, and therefore yields a significantly more informative signal (Koster H. et al., Nature Biotechnol., 14: 1123-1128 (1996)).

The production or presence of target nucleic acids and nucleic acid sequences may also be detected and monitored by various methods of gel electrophoresis. Gel electrophoresis involves the separation of nucleic acids through a matrix, generally a cross-linked polymer, using an electromotive force that pulls the molecules through the matrix. Molecules move through the matrix at different rates causing a separation between products that can be visualized and interpreted via any one of a number of methods including but not limited to; autoradiography, phosphorimaging, and staining with nucleic acid chelating dyes.

The production or presence of target nucleic acids and nucleic acid sequences may also be detected and monitored by capillary gel electrophoresis. Capillary-gel Electrophoresis (CGE) is a combination of traditional gel electrophoresis and liquid chromatography that employs a medium such as polyacrylamide in a narrow bore capillary to generate fast, high-efficient separations of nucleic acid molecules with up to single base resolution. CGE is commonly combined with laser induced fluorescence (LIF) detection where as few as six molecules of stained DNA can be detected. CGE/LIF detection generally involves the use of fluorescent DNA intercalating dyes including ethidium bromide, YOYO and SYBR Green 1 but can also involve the use of fluorescent DNA derivatives where the fluorescent dye is covalently bound to the DNA. Simultaneous identification of several different target sequences can be made using this method.

The production or presence of target nucleic acids and nucleic acid sequences may also be detected and monitored by various surface capture methods. This is accomplished by the immobilization of specific oligonucleotides to a surface producing a biosensor that is both highly sensitive and selective. Surfaces used in this method may include but are not limited to gold and carbon and may use a number of covalent or noncovalent coupling methods to attach the probe to the surface. The subsequent detection of a target DNA can be monitored by a variety of methods.

Electrochemical methods generally involve measuring the cathodic peak of intercalators, such as methylene blue, on the DNA probe electrode and visualized with square wave voltammograms. Binding of the target sequence can be observed by a decrease in the magnitude of the voltammetric reduction signals of methylene blue as it interacts with dsDNA and ssDNA differently reflecting the extent of the hybrid formation.

Surface Plasmon Resonance (SPR) can also be used to monitor the kinetics of probe attachment as well as the process of target capture. SPR does not require the use of fluorescence probes or other labels. SPR relies on the principle of light being reflected and refracted on an interface of two transparent media of different refractive indexes. Using monochromatic and p-polarized light and two transparent media with an interface comprising a thin layer of gold, total reflection of light is observed beyond a critical angle, however the electromagnetic field component of the light penetrates into the medium of lower refractive index creating an evanescent wave and a sharp shadow (surface plasmon resonance). This is due to the resonance energy transfer between the wave and the surface plasmons. The resonance conditions are influenced by the material absorbed on the thin metal film and nucleic acid molecules, proteins and sugars concentrations are able to be measured based on the relation between resonance units and mass concentration.

The production or presence of target nucleic acids and nucleic acid sequences may also be detected and monitored by lateral flow devices. Lateral Flow devices are well known. These devices generally include a solid phase fluid permeable flow path through which fluid flows through by capillary force. Examples include, but are not limited to, dipstick assays and thin layer chromatographic plates with various appropriate coatings. Immobilized on the flow path are various binding reagents for the sample, binding partners or conjugates involving binding partners for the sample and signal producing systems. Detection of samples can be achieved in several manners; enzymatic detection, nanoparticle detection, colorimetric detection, and fluorescence detection, for example. Enzymatic detection may involve enzyme-labeled probes that are hybridized to complementary nucleic aid targets on the surface of the lateral flow device. The resulting complex can be treated with appropriate markers to develop a readable signal. Nanoparticle detection involves bead technology that may use colloidal gold, latex and paramagnetic nanoparticles. In one example, beads may be conjugated to an anti-biotin antibody. Target sequences may be directly biotinylated, or target sequences may be hybridized to a sequence specific biotinylated probes. Gold and latex give rise to colorimetric signals visible to the naked eye and paramagnetic particles give rise to a non-visual signal when excited in a magnetic field and can be interpreted by a specialized reader.

Fluorescence-based lateral flow detection methods are also known, for example, dual fluorescein and biotin-labeled oligo probe methods, UPT-NALF utilizing up-converting phosphor reporters composed of lanthanide elements embedded in a crystal (Corstjens et al., Clinical Chemistry, 47:10, 1885-1893, 2001), as well as the use of quantum dots.

Nucleic acids can also be captured on lateral flow devices. Means of capture may include antibody dependent and antibody independent methods. Antibody-dependent capture generally comprises an antibody capture line and a labeled probe of complementary sequence to the target. Antibody-independent capture generally uses non-covalent interactions between two binding partners, for example, the high affinity and irreversible linkage between a biotinylated probe and a streptavidin line. Capture probes may be immobilized directly on lateral flow membranes. Both antibody dependent and antibody independent methods may be used in multiplexing.

The production or presence of target nucleic acids and nucleic acid sequences may also be detected and monitored by multiplex DNA sequencing. Multiplex DNA sequencing is a means of identifying target DNA sequences from a pool of DNA. The technique allows for the simultaneous processing of many sequencing templates. Pooled multiple templates can be resolved into individual sequences at the completion of processing. Briefly, DNA molecules are pooled, amplified and chemically fragmented. Products are fractionated by size on sequencing gels and transferred to nylon membranes. The membranes are probed and autoradiographed using methods similar to those used in standard DNA sequencing techniques (Church et al., Science 1998 Apr. 8; 240(4849):185-188). Autoradiographs can be evaluated and the presence of target nucleic acid sequence can be quantitated.

Kits

Kits of the present invention may comprise, for example, one or more polymerases, forward and reverse templates, and one or more nicking enzymes, as described herein. Where one target is to be amplified, one or two nicking enzymes may be included in the kit. Where multiple target sequences are to be amplified, and the templates designed for those target sequences comprise the nicking enzyme sites for the same nicking enzyme, then one or two nicking enzymes may be included. Or, where the templates are recognized by different nicking enzymes, more nicking enzymes may be included in the kit, such as, for example, 3 or more.

The kits of the present invention may also comprise one or more of the components in any number of separate containers, packets, tubes, vials, microtiter plates and the like, or the components may be combined in various combinations in such containers.

The components of the kit may, for example, be present in one or more containers, for example, all of the components may be in one container, or, for example, the enzymes may be in a separate container from the templates. The components may, for example, be lyophilized, freeze dried, or in a stable buffer. In one example, the polymerase and nicking enzymes are in lyophilized form in a single container, and the templates are either lyophilized, freeze dried, or in buffer, in a different container. Or, in another example, the polymerase, nicking enzymes, and the templates are, in lyophilized form, in a single container. Or, the polymerase and the nicking enzyme may be separated into different containers.

Kits may further comprise, for example, dNTPs used in the reaction, or modified nucleotides, cuvettes or other containers used for the reaction, or a vial of water or buffer for re-hydrating lyophilized components. The buffer used may, for example, be appropriate for both polymerase and nicking enzyme activity.

The kits of the present invention may also comprise instructions for performing one or more methods described herein and/or a description of one or more compositions or reagents described herein. Instructions and/or descriptions may be in printed form and may be included in a kit insert. A kit also may include a written description of an Internet location that provides such instructions or descriptions.

Kits may further comprise reagents used for detection methods, such as, for example, reagents used for FRET, lateral flow devices, dipsticks, fluorescent dye, colloidal gold particles, latex particles, a molecular beacon, or polystyrene beads.

EXAMPLES

Example 1: Detection of DNA NEAR Assay Products by Gel Electrophoresis

Figure 2:
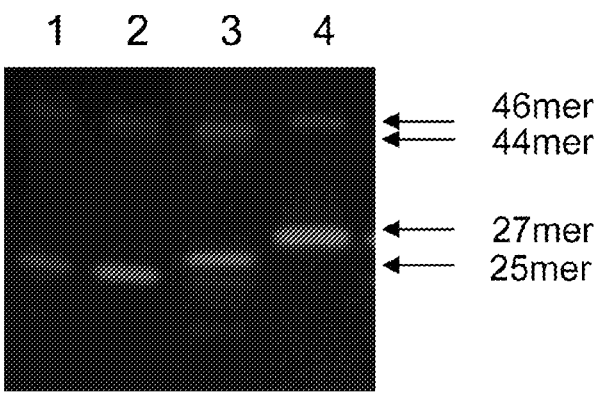
FIG. 2. 20% polyacrylamide gel of reaction products from a DNA NEAR assay.

The NEAR amplification reaction products can be visualized by gel electrophoresis. In the absence of target, the templates (with complementary 3' bases) overlap by one or more bases, polymerase extends in each direction to generate the NEAR amplification duplex (FIG. 1B); and the amplification proceeds in a similar mechanism to the NEAR amplification to amplify a product that is two bases shorter than the target amplified product. In the case of a 25 mer assay where the templates end in A and T, the resulting background product is 23 bases. The 27 mer assay also forms a 23 mer background and 27 mer product. Longer reaction products are also amplified. The sequence of these products is hypothesized to be due to the polymerase extension before the nicking enzyme can nick both sides of the NEAR amplification duplex, according to Steps 9B in FIG. 1C. FIG. 2 shows the NEAR reaction products are easily distinguished from background products by gel electrophoresis.

Example 2: Detection of RNA NEAR Assay Products by Gel Electrophoresis

The NEAR reaction can also amplify RNA targets. In this case, the target is Ebola Armored RNA, which is a ~600 base strand of RNA encapsulated by MS2 phage coat proteins to simulate a viral particle. The reaction is designed to amplify a 25-base region of the Ebola genome contained within the encapsulated RNA sequence. Reaction products run on a 20% polyacrylamide gel (FIG. 3) show the amplified 25 mer product along with 23 mer and 20 mer background products. This example demonstrates the ability of the NEAR reaction to amplify RNA released from virus-like particles.

Example 3: Detection of DNA and RNA NEAR Assay Products by Mass Spectrometry

The NEAR reaction amplification products can also be detected by mass spectrometry using an ESI/TOF system with a front end LC. The reaction products observed are multiple charged ion species. Usually, the −3 or −4 charge state is the major peak in the spectrum (in the range of 1000-3000 AMU), depending on the length of the oligonucleotide product. The sodium adduct is usually present in the spectrum as a peak adjacent to the major peak at roughly 20-25% the intensity. The unique peaks for the positive reactions in the presence of target are visible in both FIGS. 4 and 5 for the DNA and RNA NEAR reactions respectively. The background products formed in these NEAR reactions are not shown in the mass range of these spectra.

Example 4: Real-Time Detection of the NEAR Assay Amplification

The NEAR amplification reaction can also be monitored, as shown in FIG. 6, in real-time with SYBR II fluorescence. The fluorescence increases as SYBR II intercalates into the amplified double-stranded products. The background products also generate fluorescence at a slower rate than the true product. Optimization of amplification sequence, reaction temperature and reaction buffer conditions are necessary in order to visualize distinct separation between the positive reactions and the negative controls.

Example 5: FRET Detection of Real-Time NEAR Assay Amplification

NEAR amplification can also be monitored by Fluorescence Resonance Energy Transfer (FRET), as shown in FIG. 7. Amplification occurs using dual labeled templates, one on each end (5'-FAM, 3'-BHQ). Fluorescence is generated from the FAM-labeled oligonucleotide upon cleavage of the template by the nicking enzyme when it becomes double-stranded. Since fluorescence is produced by the initial nicking reaction, this detection method is extremely responsive. Since the 3' ends of the templates are blocked from extension by the quenching label, the production of background fluorescence is inhibited.

Example 6: Molecular Beacon Detection of Real-Time NEAR Amplification

A third method of monitoring real-time amplification is using molecular beacons, as shown in FIG. 8. In this case, the amplified product hybridizes to the loop region of the molecular beacon resulting in an increase in fluorescence from the separation of the fluorophore and quencher on each end of the hairpin stem. Since this interaction occurs post-amplification, it is considered pseudo-real-time and can be slightly slower in response relative to the FRET approach.

Example 7: False Alarm Rate Testing

This experiment was designed to probe the probability that the NEAR amplification reaction will yield a true product in the negative reaction, or a false positive. NEAR reactions directed at specific amplification of a 25 mer region specific to the *Bacillus subtilis* genome were run in the presence (n=120) and absence (n=320) of *Bacillus subtilis* genomic DNA. End point reactions were run on the mass spectrometer and the area under the curve (AUC) for the product mass peak in the mass spectrum was analyzed. As shown in FIG. 9, the results show that none of the 320 negative reactions resulted in a false positive with AUC values equal to the water control. The true positive AUC values were at least 3 standard deviations apart from the true negatives. Overall, these results demonstrate the reproducible nature of the NEAR assay.

Example 8: Beacon Detection

NEAR Assay Reproducibility with Beacon Detection

The molecular beacon detection of NEAR reaction products can also be used as an endpoint reading. As shown in FIG. 10, the ratio of NEAR reaction products can be manipulated by varying the input ratio of the forward and reverse templates. Skewing the templates to favor one of the reaction products allows the single-stranded product to be available for hybridization to a molecular beacon. The open beacon generates a fluorescent signal. This detection method is extremely reproducible. In this study, two operators performed replicates of the same assay on two different days. The results of this study demonstrate the reproducibility of the assay from one day to the next as well as reproducibility between operators.

Example 9: NEAR Assay Sensitivity with Beacon Detection

The sensitivity of the NEAR assay with beacon read-out was tested using a dilution of *Francisella tularensis* genomic DNA. As shown in FIG. 11, as few as 50 copies were detected above the no target control.

Example 10: Concentration of Amplified Products for NEAR DNA Amplification

The sensitivity of the NEAR assay has also been studied using mass spectrometry detection of the reaction products. FIG. 12 shows signal above the no target control down to 100 copies. The data from this study was used to correlate the input copy number to the final amount of amplified product. In this study, the AUC values of the mass spec product peaks were fit to a standard curve to give the estimated final concentration of amplified product for the NEAR assay. The amount of amplified product ranges from approximately 250 nM to almost 1 µM for 1E+2 and 1E+5 copies respectively. This product amount results in a 1E+8 to 7E+10-fold amplification. These reactions were performed without the hot-start conditions, in fact hot-start conditions have been shown to dramatically increase the amount of product amplified, so a further increase in amplification is achieved. The zero copy amplification reaction has a positive final concentration due to the y-intercept value in the standard curve equation.

Example 11: Concentration of Amplified Products for RNA Assay

A similar study was performed on the NEAR amplification of RNA. A dilution of RNA targets were amplified by the NEAR assay. Products were run on the mass spec and the AUC values of the product peaks were analyzed against a standard curve to determine the concentration of the final product, as shown in FIG. 13. A 12 minute amplification starting with 30 and 30,000 copies of initial target results in a 3E+9 to 1E+7-fold amplification respectively. The lower extent of amplification compared to the DNA amplification could be due to the less efficient reverse transcriptase ability of the polymerase compared to its replication abilities. Also, the RNA:DNA hybrid formed upon the extension of the reverse template is a stronger interaction compared to a normal DNA:DNA hybrid and will have less breathing to allow for the forward or another reverse template to displace one strand. However, amplification products from the RNA reaction were detected down to <100 copies.

Example 12: NEAR Reaction Specificity for DNA

Since the reaction products are usually between 20 and 30 bases in length, the question arises as to whether or not these short amplification assays can be specific enough to target a single sequence region with other near neighbor genomes present. The NEAR reaction was tested for its specificity by running the amplification reaction in the presence and absence of varying amounts of the near neighbor genomic DNA (FIG. 14). In this case, the assay detects a specific sequence in the pXO2 plasmid of *Bacillus anthracis* and the near neighbor genome is *Bacillus thuringiensis* (kurstaki). The reactions were analyzed by the AUC values for the product peaks. The figure below demonstrates that in the absence of the correct target (*Bacillus anthracis*), there is no true product amplified (the levels are so low that they are not visible on the scale of the graph). The amount of amplification of the positive reactions is consistent, with larger error bars for the 0 and 5E+5 copies of *Bacillus thuringiensis* (5E+4 copies of *Bacillus anthracis*) due to a single lower value for one of the triplicate runs. Overall the experiment demonstrates that the NEAR reaction is very specific to the target sequence when the assay is designed within a unique region of the genome.

Example 13: Interferent Testing

A panel of interferents was tested to monitor the effect of each on the NEAR assay amplification. FIG. 15 demonstrates the robust nature of the NEAR assay in the presence of interferents. Some interferents that are known to inhibit PCR, such as humic acid, did not appear to inhibit the NEAR assay, though the amount of each interferent is unknown. From statistical analysis only interferent B, C, and E were statistically different from the control assay x. In the B, C, and E cases, the difference resulted in increased product amplification.

Example 14: Multiplexing of Two Sequences with NEAR DNA Assays

A DNA duplex was designed for capillary electrophoresis (CE) detection. Amplification products were 25 bases (*Bacillus anthracis* assay, Ba) and 27 bases (*Bacillus subtilis* assay, Bs) in length with background production of a 23 mer. The reaction was run for 10 minutes in the presence or absence of 5E+5 copies of the respective genomic DNA target. The samples were run on a 20% polyacrylamide gel to visualize the reaction products. FIG. 16 indicates the presence of positive product amplification when *Bacillus subtilis* only is present as well as when both *Bacillus subtilis* and *Bacillus anthracis* are present.

Example 15: NEAR DNA Assay Duplex Specificity

The NEAR DNA duplex reaction with *Bacillus subtilis* (Bs) and *Bacillus anthracis* (Ba) was shown to be specific to the respective genomes. The assays were run in the presence of the near neighbor, *Bacillus thuringiensis*, as shown in FIG. 17. In the negative reaction where both template sets are present as well as the *Bacillus thuringiensis* genomic DNA, there is no product band in the 25 or 27 mer region. Product bands appear only when the specific genomic target is present, which demonstrates the specificity of the duplex reaction.

Example 16: Multiplexing with NEAR RNA Assays

An MS2 assay that amplifies a 27 mer product and an Ebola assay that amplifies a 25 mer product was developed and multiplexed so that all templates are present in each assay and amplification of products is dependent on the target present. This combination of templates forms background products that are 23 bases and 20 bases in length. The gel shown in FIG. 18 demonstrates the ability for the NEAR reaction to amplify multiple RNA targets in a single reaction.

Example 17: Amplification from Lysed Spores by NEAR Assay

Amplification was performed on semi-processed samples to determine whether it is possible to amplify DNA released from spores through lysis. The negative control reaction contained DNase-treated spores, unlysed, so no DNA should be present to amplify. The positive control reaction contained purified genomic DNA at concentrations around the amount of DNA estimated to be released through lysis. Results in FIG. 19 show that amplification with unlysed DNase-treated spores results in no product amplification as expected, whereas the three samples lysed before amplification resulted in product amounts in the range of the theoretical amounts.

Example 18: Capture and Extension

The NEAR reaction products can also be detected on a solid surface. A capture probe attached at the 5' end to the surface through a biotin/streptavidin attachment can bind to the reaction products from which polymerase extends to form a stable duplex that SYBR and any intercalating dye can detect. The capture probe is designed to favor extension through binding to the true product over background products because the 3' base of the capture probe is complementary to the middle spacer base in the product which is not present in either of the templates or the background products. FIG. 20 demonstrates the increased fluorescence of the NEAR products in the presence of the capture probe and polymerase over the average binding (same reaction in the absence of polymerase, to preclude extension of the capture probe) and the no target control where only background products are amplified, but cannot form a stable duplex with the capture probe for polymerase to extend.

Example 19: Surface NEAR FRET DNA Assay

The NEAR reaction can also be performed with the templates immobilized on the surface. The templates for FRET detection of surface amplification usually have three modifications: one 5' biotin with a TEG spacer, one FAM fluorophore internal to the biotin, and a quencher on the 3' end which serves to block background amplification as well as to quench the FAM fluorophore. The template is immobilized on the surface through biotin/streptavidin attachment. FIG. 21 demonstrates that with both templates immobilized along with additional mixing, the reaction proceeds at a much slower rate than the solution amplification rate (amplification in 16 minutes for 1E+6 copies of genomic DNA). When a single template is immobilized on the surface and the other template is free in solution, the amplification reaction is increased to 10 minute detection for 1E+6 copies of genomic DNA. Fluorescence from background products is observed ~3.5 minutes after the product signal, similar to what is observed for solution phase kinetics, but slowed considerably.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Singular forms "a", "an", and "the" include plural reference unless the context clearly dictates otherwise. Thus, for example, reference to "a subset" includes a plurality of such subsets, reference to "a nucleic acid" includes one or more nucleic acids and equivalents thereof known to those skilled in the art, and so forth. The term "or" is not meant to be exclusive to one or the terms it designates. For example, as it is used in a phrase of the structure "A or B" may denote A alone, B alone, or both A and B.

Unless defined otherwise, all technical and scientific terms used herein have the same meanings as commonly understood by one of ordinary skill in the art to which this invention belongs. Although any methods and systems similar or equivalent to those described herein can be used in the practice or testing of the present invention, the methods, devices, and materials are now described. All publications mentioned herein are incorporated herein by reference for the purpose of describing and disclosing the processes, systems, and methodologies that are reported in the publications which might be used in connection with the invention. Nothing herein is to be construed as an admission that the invention is not entitled to antedate such disclosure by virtue of prior invention.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

What is claimed is:

1. A method for amplifying a double-stranded nucleic acid target sequence, comprising:
   a) contacting a target DNA molecule comprising a double-stranded target sequence having a sense strand and an antisense strand, without, prior to the contacting, subjecting the target DNA molecule to a thermal denaturation step associated with amplification of the target sequence, with:
   (1) a forward template and a reverse template, wherein
      i) said forward template comprises a nucleic acid sequence comprising a recognition region at the 3' end that is complementary to the 3' end of the target sequence antisense strand; a nicking enzyme binding site and a nicking site upstream of said recognition region; and a stabilizing region upstream of said nicking site, wherein the portion of the nucleic acid sequence that is complementary to the 3' end of the target antisense strand is 8-15 nucleotides in length; wherein when the recognition region of the forward template is hybridized to the target sequence, the stabilizing region of the forward template is not hybridized to the target nucleic acid molecule;
      ii) said reverse template comprises a nucleotide sequence comprising a recognition region at the 3' end that is complementary to the 3' end of the target sequence sense strand; a nicking enzyme binding site and a nicking site upstream of said recognition region, and a stabilizing region upstream of said nicking site, wherein the portion of the nucleic acid sequence that is complementary to the 3' end of the target sense strand is 8-15 nucleotides in length; wherein when the recognition region of the reverse template is hybridized to the target sequence, the stabilizing region of the reverse template is not hybridized to the target nucleic acid molecule;
   (2) a first nicking enzyme that is capable of nicking at the nicking site of said forward template, and does not nick within said target sequence;
   (3) a second nicking enzyme that is capable of nicking at the nicking site of said reverse template and does not nick within said target sequence;
   (4) a DNA polymerase; and
   b) amplifying the double-stranded nucleic acid target sequence under essentially isothermal conditions; wherein amplification is performed by multiple cycles of said polymerase extending said forward and reverse templates along said target sequence producing a double-stranded nicking site, and said nicking enzymes nicking at said nicking sites, and, following a first round of amplification, at amplified copies of said sites, producing an amplification product.

2. The method of claim 1, wherein said DNA polymerase is a thermophilic polymerase.

3. The method of claim 1, wherein said polymerase is selected from the group consisting of Bst (large fragment), and exo-DNA Polymerase.

4. The method of claim 1, wherein said polymerase is Bst (large fragment).

5. The method of claim 1, wherein said nicking enzymes nick downstream of the nicking enzyme binding site.

6. The method of claim 1, wherein said forward and reverse templates comprise nicking enzyme binding sites recognized by the same nicking enzyme and said first and said second nicking enzymes are the same.

7. The method of claim 1, wherein said nicking enzymes are selected from the group consisting of Nt.BspQI, Nb.BbvCi, Nb.BsmI, Nb.BsrDI, Nb.BtsI, Nt.AlwI, Nt.BbvCI, Nt.BstNBI, Nt.CviPII, Nb.Bpu10I, and Nt.Bpu10I.

8. The method of claim 1, wherein said target sequence comprises 1 nucleotide more than the sum of the nucleotides of said forward template recognition region and said reverse template recognition region.

9. The method of claim 1, wherein said target sequence comprises 2 nucleotides more than the sum of the nucleotides of said forward template recognition region and said reverse template recognition region.

10. The method of claim 1, wherein the target DNA molecule is selected from the group consisting of genomic DNA, plasmid, mitochondrial, and viral DNA.

11. The method of claim 1, wherein the forward template is provided at the same concentration as the reverse template.

12. The method of claim 1, wherein the amplification is conducted between 54° C. and 60° C.

13. The method of claim 1, wherein the amplification reaction is held at a constant temperature for 1 to 10 minutes.

14. The method of claim 1, further comprising detecting the amplification product.

15. The method of claim 1, wherein said amplification product is detected by a method selected from the group consisting of gel electrophoresis, mass spectrometry, intercalating dye detection, FRET, molecular beacon detection, surface capture, capillary electrophoresis, incorporation of labeled nucleotides to allow detection by capture, fluorescence polarization, and lateral flow capture.

16. The method of claim 1, wherein the method comprises amplifying at least two target sequences.

* * * * *

UNITED STATES PATENT AND TRADEMARK OFFICE
CERTIFICATE OF CORRECTION

PATENT NO. : 9,689,031 B2  
APPLICATION NO. : 11/778018  
DATED : June 27, 2017  
INVENTOR(S) : Brian K. Maples et al.

Page 1 of 1

It is certified that error appears in the above-identified patent and that said Letters Patent is hereby corrected as shown below:

In the Claims

Column 32, Line 58, Claim 15, after "spectrometry," insert -- fluorescence, --

Signed and Sealed this  
Fifth Day of September, 2017

Joseph Matal  
*Performing the Functions and Duties of the*  
*Under Secretary of Commerce for Intellectual Property and*  
*Director of the United States Patent and Trademark Office*